(12) United States Patent
Koptenko

(10) Patent No.: US 11,154,276 B2
(45) Date of Patent: Oct. 26, 2021

(54) ULTRASOUND BEAMFORMING SYSTEM AND METHOD WITH RECONFIGURABLE APERTURE

(71) Applicant: URS-US MEDICAL TECHNOLOGY INC., Pittsburgh, PA (US)

(72) Inventor: Sergei Koptenko, Mississauga (CA)

(*) Notice: Subject to any disclaimer, the term of this patent is extended or adjusted under 35 U.S.C. 154(b) by 573 days.

(21) Appl. No.: 16/011,321

(22) Filed: Jun. 18, 2018

(65) Prior Publication Data

US 2019/0133556 A1    May 9, 2019

Related U.S. Application Data

(63) Continuation of application No. PCT/US2016/067521, filed on Dec. 19, 2016.
(Continued)

(51) Int. Cl.
*A61B 8/00* (2006.01)
*G01S 7/52* (2006.01)
(Continued)

(52) U.S. Cl.
CPC .............. *A61B 8/4494* (2013.01); *A61B 8/00* (2013.01); *A61B 8/145* (2013.01); *A61B 8/54* (2013.01);
(Continued)

(58) Field of Classification Search
CPC ........... A61B 8/00; A61B 8/4494; A61B 8/54; A61B 8/145; G01S 7/52034;
(Continued)

(56) References Cited

U.S. PATENT DOCUMENTS 4,058,003 A * 11/1977 Macovski ............ G10K 11/346
73/626
4,127,034 A * 11/1978 Lederman .............. G01N 29/06
367/7
(Continued)

OTHER PUBLICATIONS

A.R.,, Kino, G.S., Khuri-Yakub, B.T., "A theory for the radiation pattern of a narrow-strip acoustic transducer", Appl. Phys. Lett., 37(1), Jul. 1, 1980, pp. 35-36.).
(Continued)

*Primary Examiner* — Oommen Jacob
(74) *Attorney, Agent, or Firm* — Blynn L. Shideler; Krisanne Shideler; BLK Law Group

(57) ABSTRACT

An ultrasound imaging system beamforming method comprises reconfiguring the aperture at distinct beamforming instances by i) Increasing the number of channels forming the aperture at a beam forming instance while simultaneously decreasing the sampling rate with an increasing depth of focal point; ii) Increasing the number of array elements that are part of a composite element of a channel forming the aperture at a beam forming instance with an increasing depth of focal point, wherein a composite element is a plurality of individual array elements forming a single channel at a beam forming instance; and/or iii) Defining allowable delay error for each depth of focal point and selecting a base channel for each beamforming instance to form the aperture and selecting additional channels to form the aperture at the beam forming instance which have a delay error relative to the base channel less than the allowable delay error.

15 Claims, 13 Drawing Sheets

Related U.S. Application Data

(60) Provisional application No. 62/269,567, filed on Dec. 18, 2015.

(51) Int. Cl.
  *G10K 11/34* (2006.01)
  *G01S 15/89* (2006.01)
  *A61B 8/14* (2006.01)

(52) U.S. Cl.
  CPC ...... *G01S 7/52025* (2013.01); *G01S 7/52034* (2013.01); *G01S 15/8927* (2013.01); *G10K 11/34* (2013.01); *G10K 11/346* (2013.01)

(58) Field of Classification Search
  CPC ............. G01S 15/8927; G01S 7/52025; G01S 7/52079–52084; G01S 7/52085–52095; G01S 15/8925–8927; G01S 7/52023; G01S 15/8915; G10K 11/34; G10K 11/346
  See application file for complete search history.

(56) References Cited

U.S. PATENT DOCUMENTS

| | | | | |
|---|---|---|---|---|
| 4,167,753 A * | 9/1979 | Lynk | ................... | G01S 7/52026 348/163 |
| 4,180,790 A | 12/1979 | Thomas | | |
| 4,330,875 A * | 5/1982 | Tachita | ............... | G01S 7/52046 367/105 |
| 4,694,700 A * | 9/1987 | Maerfeld | ............ | G01S 7/52063 73/625 |
| 4,829,491 A * | 5/1989 | Saugeon | .............. | G10K 11/346 367/103 |
| 4,839,652 A * | 6/1989 | O'Donnell | .......... | G01S 7/52046 327/94 |
| 5,555,534 A * | 9/1996 | Maslak | ................ | G01S 15/8927 367/135 |
| 5,590,659 A * | 1/1997 | Hamilton | ................. | G01S 7/295 600/447 |
| 5,722,412 A | 3/1998 | Pflugrath et al. | | |
| 5,817,024 A | 10/1998 | Ogle et al. | | |
| 5,928,152 A * | 7/1999 | Wright | ................ | G01S 15/8988 600/447 |
| 6,106,472 A | 8/2000 | Chiang et al. | | |
| 6,120,449 A * | 9/2000 | Snyder | ................... | G01S 7/5205 600/447 |
| 6,679,845 B2 * | 1/2004 | Ritter | ................... | G01S 7/52046 600/444 |
| 6,869,401 B2 | 3/2005 | Gilbert et al. | | |
| 7,115,093 B2 | 10/2006 | Halmann et al. | | |
| 8,033,172 B2 * | 10/2011 | Langlois | .............. | G01N 29/069 73/626 |
| 8,137,280 B2 * | 3/2012 | Angelsen | ............ | G01S 7/52025 600/459 |
| 9,739,875 B2 * | 8/2017 | Koptenko | ........... | G01S 7/52023 |
| 2009/0326375 A1 * | 12/2009 | Magee | ................. | G10K 11/346 600/443 |
| 2012/0143059 A1 * | 6/2012 | Magee | ................ | G01S 7/52047 600/447 |
| 2012/0323121 A1 | 12/2012 | Miller | | |

OTHER PUBLICATIONS

McKeighen, R.E., "Design Guidelines for Medical Ultrasonic Arrays", SPIE International Symposium on Medical Imaging, Feb. 25, 1998, San Diego.

Ming Yang—Separable Beamforming for 3-D Medical Ultrasound Imaging vol. 63 No. 2 Jan. 15, 2015.

Wei Jiang—Ultrasound Focusing by Use of Apertures w Different Pitches and Ultrasound Imaging by Use of a Hemispheric Transducer Array, University of Rochester, Rochester, New York, 2011.

* cited by examiner

ULTRASOUND BEAMFORMING SYSTEM AND METHOD WITH RECONFIGURABLE APERTURE

RELATED APPLICATION

This application is a continuation of PCT/US2016/067521 filed Dec. 19, 2016 and that published Jun. 22, 2017 as WO 2017/106,834, which publication and application are incorporated herein by reference.

PCT/US2016/067521 claims the benefit of U.S. Provisional Patent Application Ser. No. 62/269,567 filed Dec. 18, 2015 and entitled "Ultrasound Beamforming with Reconfigurable Aperture System and Method" which application is incorporated herein by reference.

BACKGROUND INFORMATION

1. Field of the Invention

The present invention relates to ultrasonic beamforming, specifically the present invention relates to ultrasound imaging and, more specifically to a digital ultrasound medical imaging beamforming system and associated method.

2. Background of the Invention

Medical ultrasound imaging, also known as diagnostic sonography or ultrasonography, is an effective, safe and relatively inexpensive diagnostic tool widely used in variety of clinical applications. It is used to see internal body structures such as tendons, muscles, joints, vessels and internal organs. Its aim is often to find a source of a disease or to exclude any pathology. The practice of examining pregnant women using ultrasound is called obstetric ultrasound, and is widely used. Ultrasound is sound waves with frequencies which are higher than those audible to humans (>20,000 Hz). Ultrasonic images also known as sonograms are made by sending pulses of ultrasound into tissue using a probe. The sound echoes off the tissue; with different tissues reflecting varying degrees of sound. These echoes are recorded and displayed as an image to the operator.

The performance of ultrasound imaging devices heavily depend on the complexity of hardware and software components of ultrasonic equipment, thus, many advanced diagnostic capabilities can be found only in fairly expensive and bulky premium systems. Over the years, remarkable improvements in imaging resolution and quality may be observed, resulting in the appearance of new imaging capabilities and new application areas where the diagnostic ultrasound excels.

One aspect of this evolution of diagnostic ultrasound systems is the constant migration of advances in imaging capabilities from premium systems down to mid-range and low cost systems. Another aspect of ultrasound systems evolution worth mentioning is the continuous efforts to reduce the hardware dimensions and the dissipated power of the systems. This is especially significant for the portable digital beamformer ultrasound systems due to the cost associated with a beamformer channel in digital beamforming architecture. Illustrating this point, consider how a typical ultrasound diagnostic system operates described below in connection with FIG. 1.

The process of medical diagnostic ultrasound imaging begins with sending specially constructed ultrasonic signals (pulses, waves or wave packets) into the tissues. The pressure pulse propagates in depth while attenuating by tissues and scattering on the acoustic impedance interfaces (such as a boundary between different tissues) along the way. These scattered echoes are picked up by the receiving ultrasound array and from this data the tissue signature along the pulse propagation path is reconstructed as a single scan line. Then, the next pulse is sent in the same or different direction (selected by the process control algorithm) and the process of receiving scattered ultrasound signals back to the sensor array (or attenuated as in transmission tomography), is repeated until a required 2-D slice (i.e. B-mode frame—most common) or a 3-D volume is assembled out of separate scan lines.

In order to increase the spatial and contrast (magnitude) resolution of a signal coming from the certain spatial location within the tissue, the ultrasound array needs to be focused on that location. Thus, in the course of pressure pulse propagation in the tissue, the receiving array needs to constantly shift its focus following the pulse current position. Therefore, one of the first steps in processing the raw data is called beamforming in which signals coming to different elements of the array are time-shifted before they will be added to one another. As a rule, the beamforming applies to both, transmit and receive signals.

The principles of dynamic aperture and focus control is described, for instance, in GE's (now GE Healthcare) U.S. Pat. No. 4,180,790 from the late 70s entitled "Dynamic array aperture and focus control for ultrasonic imaging systems" which patent is incorporated herein by reference and the teachings of which may be considered to serve as an effective model for all subsequent developments in digital beamformer systems. FIG. 1 illustrates the widely spread method used in forming ultrasound images, also known as digital beamforming.

Generally, the ultrasound imaging device consists of an ultrasonic array 106 divided to a number of independent elements 107, typically having 64 elements in phased array and from 128 to 256 elements in linear or curved 1D array. During the transmit stage of interrogation, the transmit beamformer sends variably delayed electric pulses to the elements of the ultrasound array 106. The relative delays between the signals is constructed in such a way that ultrasonic pulses emitted by elements 107 of the array 106 would arrive to the predetermined spatial point 100 (focal point P) simultaneously, with their phases aligned to achieve a coherent summation of wavelets coming from all elements 107 of the array 106. This wave would scatter at tissue in-homogeneities at the point 100 and part of this spherical scattered wave would travel back to the elements 107 of the array 106. Each element 107 would convert pressure variations in the incoming wave into the voltage variation output 108. The portion of this scattered wave that reaches a face surface of an array element 107 can be seen as a wavelet 102 that travels along the ray 104 that connects the scattering point 100 and the face of the element 107.

Depending on the mutual position of the scattering point 100 and the specific element 107 of the array 106, the path 104 would vary from the shortest one equivalent to radius RO 105 to the longest one 118. The spatial difference $\Delta D_i$ between the shortest path 105 and path from the point 100 to the i-element of the array 106 translates into the time delay $\Delta t_i$ between the arrivals of signals 108. The task of the receive beamformer is to modify the time differences between the signals 108 from all elements 107 participating in beamforming and sum them in accordance with the directions of the beamforming algorithm. For example, such a beamforming algorithm may require removing the time delays $\Delta t$ from all arrived signals and sum such processed signals (delay-sum algorithm), in effect focusing the array to the point P. It can be seen that workings of transmit and receive beamformers are mutually reciprocal, thus, describing the works of the receive beamformer also would describe the solutions for the transmit beamformer.

In the ultrasound beamformer, voltage signals 108 from the elements of the array 106 may pass through a number of electronic circuitry blocks (also known as analog front-end) such as filters, analog switches, multiplexors, linear, and buffer preamplifiers, that for the sake of clarity are omitted on the FIG. 1 excepting the block 110—Voltage Controlled Amplifier (VCA). The signals coming from the elements 107 are amplified by the voltage controlled amplifier (VCA) 110 to compensate the signal attenuation, then, the signal in each channel is digitized at a certain sampling rate by channel ADC 112 that outputs digitized signal to the memory or First-In-First-Out (FIFO) registers 114 where digital representation of the signals are manipulated in accordance with the beamforming algorithm (for example— shifted, such that to remove arrival delay $\Delta t$), then such processed digital data 116 from each participating channel are summed by digital adder 120 and output data 122 are written to the memory for further processing. The advantages of digital beamformer, such as shown in FIG. 1, are its speed and precision which allows implementation of the dynamic beamforming and the possibility of realization of multiple beamforming strategies on the same data volume. The disadvantage is complexity of the hardware; manifesting in larger hardware size, higher cost, and higher power consumption (heat generation).

For the reasons of clarity, the beamforming schematic for digital beamformers shown on FIG. 1 was simplified by removing the multiplexing stage. Further, in all descriptions and schematic diagrams the placement of elements or blocks such as VCA, LNA, voltage followers switches, etc. that are secondary to the understanding of the invention are not strictly followed, assuming that anybody with ordinary knowledge of electronic design would understand their functions would determine where they should be placed in the actual working schematics, their structure, and parameters.

As known to those of ordinary skill in the art, having the number of processing channels equal to the number of the arrays' elements is an expensive proposition citing above-mentioned disadvantages. Thus, in many portable and low cost ultrasound devices the array can have 64, 128, 256 or greater number of elements but the beamformer itself would have lesser number of beamforming channels, typically 32 or 64 channels and have an analog multiplexing circuitry that would assemble groups of elements of the array 106 into the current transmit-receive aperture. Also for the same reasons, cable and signal connectors that connect elements of array 106 to the analog front-end electronics are not shown, even though they do affect the cost and signal quality of the system.

From the above description of the beamforming process it can be seen that the signal coming from the output of the array element 107 is processed independently from the signals coming from the other elements up to the output of the beamformer where all of the signals are combined. Thus, this text will refer to this signal path from the element 107 to the input of adder 120 as a "signal path" or "beamforming channel" or simply as "channel" 109.

The emergence of certain healthcare modes, like "point-of-care concepts", as well as expansion of more traditional areas of application of portable ultrasound such as emergency departments drives the need for better portable and inexpensive ultrasound systems as numerous prior art solutions may testify. For example, SonoSight, Inc.'s U.S. Pat. Nos. 5,722,412 and 5,817,024 depict a hand held ultrasonic diagnostic device capable of performing B-mode and Doppler imaging having a digital beamformer implemented on an integrated chip or an ASIC. Teratech Corporations's U.S. Pat. No. 6,106,472, entitled "Portable ultrasound imaging system" describes the design of a beamformer circuit as charge coupled device, and GE Medical System Global Technology Company, LLC's U.S. Pat. No. 7,115,093 entitled "Method and system for PDA-based ultrasound system" outlines an inexpensive hand-held ultrasound system that communicates with an off-the-shelf personal digital assistant device (PDA) through a standard digital interface, and Teratech Corporations's U.S. Pat. No. 6,869,401 "Ultrasound probe with integrated electronics" describes a handheld ultrasound system with beamformer electronics being integrated within a probe enclosure. There more similar patents, not listed herein for reasons of space, that expound numerous strategies to minimize the ultrasound beamformer's circuitry size and power consumption in order to fit it within the form-factor of a portable or hand-held device while producing the diagnostic quality of imaging acceptable to the user.

The diagnostic quality of ultrasound imaging, its contrast and detail resolution, among other things, critically depends on the size of the aperture, number of parallel beamforming channels, digitization resolution of an analog to digital converter (ADC) in the beamformer channel, and ADC sampling rate. In order to fit such a beamformer and associated circuitry into portable of hand-held format, a serious reduction of beamformer circuitry complexity must be achieved. Typically, it is done by reducing the number of parallel beamforming channels or/and ADC dynamic range or sampling rate with corresponding reductions in image quality or frame rate or other undesirable consequences which should be avoided.

Another previous attempts to optimize the aperture configuration and sampling time are described in Toshiba Medical System Corporation's US Patent Application 2012-0323121A1 entitled "Variable power saving processing scheme for ultrasound beamformer functionality" that outlines a power saving scheme through the intelligent channel turn on/off and sampling time decrease with depth via ADC clock adjustments. Another approach is described in SURF Technology AS's U.S. Pat. No. 8,137,280 entitled "Digital ultrasound beam former with flexible channel and frequency range reconfiguration" which describes a digital ultrasound beamformer where the beamformer's front-end can be configured for different sampling rates and number of channels in the aperture depending on the type of the array used and desirable frequency bandwidth and channel's ADC sample rate is adaptable to an actual received ultrasound frequency band.

Texas Instruments Inc.'s U.S. Patent Pub. No. 2012-0143059 was cited in WO 2017/106,834 is directed to methods of apodization for ultrasound beamforming, ultrasound imaging systems therefrom, and hardware such as digital signal processors (DSPs) for implementing ultrasound imaging blocks and functions including the filter block, apodization block, dynamic aperture control block, controller, and summer. Digital channel data representing echo data from target tissue in a plurality (k) of data channels and a predefined number (less than or equal to k) of active channels ($N_{act}$) selected from the plurality of data channels are provided. A software-based integrated apodization algorithm dynamically apodizes the digital channel data using a selected apodizing function h[n,k]. The integrated apodization algorithm applies dynamic aperture control to create an effective aperture by generating a parameter numAperture-Channels ($N_{ap}[n]$), where $N_{ap}[n,k]$ is less than or equal to $N_{act}$, and selecting $N_{ap}[n]$ particular ones of the data channels based on a dynamic beam focusing location for ultrasound beamforming. Applied dynamic data scaling provides data normalization using a vector inner product between h[n,k] and a scale factor to generate the normalized apodization factors $h_{norm}[n,k]$.

All of the above identified patents and published patent applications are incorporated herein by reference. There remains a need in the art to reduce the size and power requirements of diagnostic ultrasound imaging and to utilize beamforming architecture to accomplish this goal without sacrificing the diagnostic image quality.

SUMMARY OF THE INVENTION

This invention preserves diagnostic quality of ultrasound in portable or handheld configuration in terms of spatial and contrast resolution through the dynamic optimization of aperture configuration and intelligent control of the sampling rate of a beamformer channel. The architecture provides significant reduction in power consumption and reduction in the size of the system while preserving and improving the image quality.

One aspect of the invention provides an ultrasound beamforming method with reconfigurable aperture for an ultrasound imaging system comprising the steps of: A) Providing an ultrasonic array formed of individual ultrasonic array elements configured for transmission and receiving; B) Dividing a subset of the individual array elements into a plurality of individual channels forming an aperture associated with a focal point of a specific depth for a beamforming instance, wherein each channel comprises at least one array element; C) Creating a signal for each channel forming an aperture associated with a focal point of a specific depth for a beamforming instance; D) Sampling, at a sampling rate, the signals of the channels forming an aperture associated with a focal point of a specific depth for a beamforming instance; and E) Reconfiguring the aperture at distinct beamforming instances by at least one of i) Increasing the number of channels forming the aperture at a beam forming instance with an increasing depth of focal point while simultaneously decreasing the sampling rate with an increasing depth of focal point; ii) Increasing the number of array elements that are part of a composite element of a channel forming the aperture at a beam forming instance with an increasing depth of focal point, wherein a composite element is a plurality of individual array elements forming a single channel at a beam forming instance; and iii) Defining allowable delay error for each depth of focal point and selecting a base channel for each beamforming instance to form the aperture and selecting additional channels to form the aperture at the beam forming instance which have a delay error relative to the base channel less than the allowable delay error.

One aspect of the invention provides an ultrasound beamforming system with reconfigurable aperture for an ultrasound imaging comprising: an ultrasonic array formed of individual ultrasonic array elements configured for transmission and receiving and a control configured for A) dividing a subset of the individual array elements into a plurality of individual channels forming an aperture associated with a focal point of a specific depth for a beamforming instance, wherein each channel comprises at least one array element, B) Creating a signal for each channel forming an aperture associated with a focal point of a specific depth for a beamforming instance, C) Sampling, at a sampling rate, the signals of the channels forming an aperture associated with a focal point of a specific depth for a beamforming instance, and E) Reconfiguring the aperture at distinct beamforming instances by at least one of i) Increasing the number of channels forming the aperture at a beam forming instance with an increasing depth of focal point while simultaneously decreasing the sampling rate with an increasing depth of focal point; ii) Increasing the number of array elements that are part of a composite element of a channel forming the aperture at a beam forming instance with an increasing depth of focal point, wherein a composite element is a plurality of individual array elements forming a single channel at a beam forming instance; and iii) Defining allowable delay error for each depth of focal point and selecting a base channel for each beamforming instance to form the aperture and selecting additional channels to form the aperture at the beam forming instance which have a delay error relative to the base channel less than the allowable delay error.

These and other advantages of the present invention will be clarified in the brief description of the preferred embodiment taken together with the drawings in which like reference numerals represent like elements throughout.

DESCRIPTION OF THE PREFERRED EMBODIMENTS

The present invention relates to ultrasound diagnostic systems, such as used in medical diagnostic systems for medical human and animal applications. The present invention described herein preserves diagnostic quality of ultrasound in portable or handheld configuration in terms of spatial and contrast resolution through the dynamic optimization of aperture configuration and intelligent control of the sampling rate of a beamformer channel.

The present invention builds upon the presumed principle that the size of the aperture L defines the spatial resolution of the ultrasound scanner at depth D (as F-number=D/L) where bigger aperture provides a better resolution. The optimal size of the aperture in ultrasound scanning is defined by the array's element own directivity (see Selfridge, A. R., Kino, G. S., Khuri-Yakub, B. T., "A theory for the radiation pattern of a narrow-strip acoustic transducer", Appl. Phys. Lett., 37(1), 1 Jul. 1980, pp. 35-36). The desired turn-on rate of beamformer channels as function of individual element's angular sensitivity and cut-off criteria can be calculated for instance following McKeighen, R. E., "Design Guidelines for Medical Ultrasonic Arrays", SPIE International Symposium on Medical Imaging, Feb. 25, 1998, San Diego, thus, the size of the aperture increases with depth from smallest aperture at shallow depth and maximum aperture at large depth.

A second operational principle for the present invention related to the size of the aperture is that the contrast resolution at small depth needs fewer elements because return signals are strong, but at deeper end it needs larger aperture to collect weak signals.

A third operational principle for the present invention is that, due to the frequency dependent attenuation, the spectral content of the return signal changes with depth, such that while it is feasible to digitize the return signals at high sampling rate when sample comes from the shallow depth, the sampling rate can be decreased in accordance with the increasing depth from which scattered ultrasound signals return without much loss to the quality of captured signal.

The forth operational principle of the present invention is that, contrary to the popular belief, the optimal sampling rate in a beamformer channel is defined not by the Nyquist criterion (often stated as $f_s > 2B$ where $f_s$ is the sampling rate and B is the bandwidth of the signal) but by the more stringent requirement to minimize the focusing delay errors (or delay quantization errors) during the channels summation in the process of beamforming.

Figure 1:
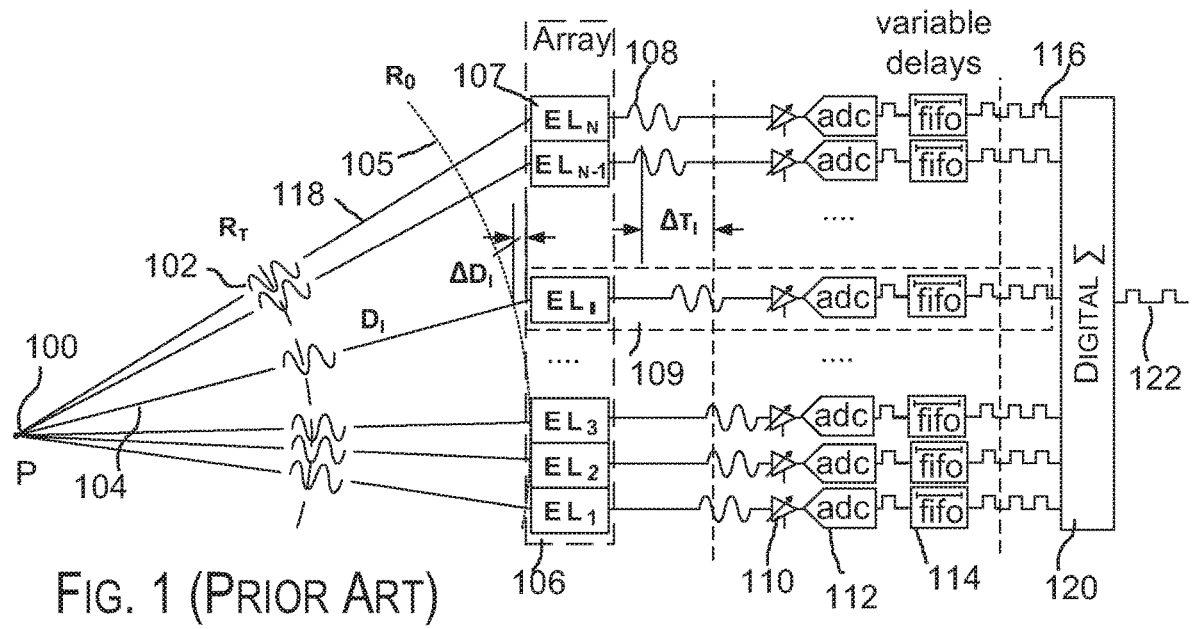
FIG. 1 is a schematic representation of a prior art digital beamformer.
Figure 2:
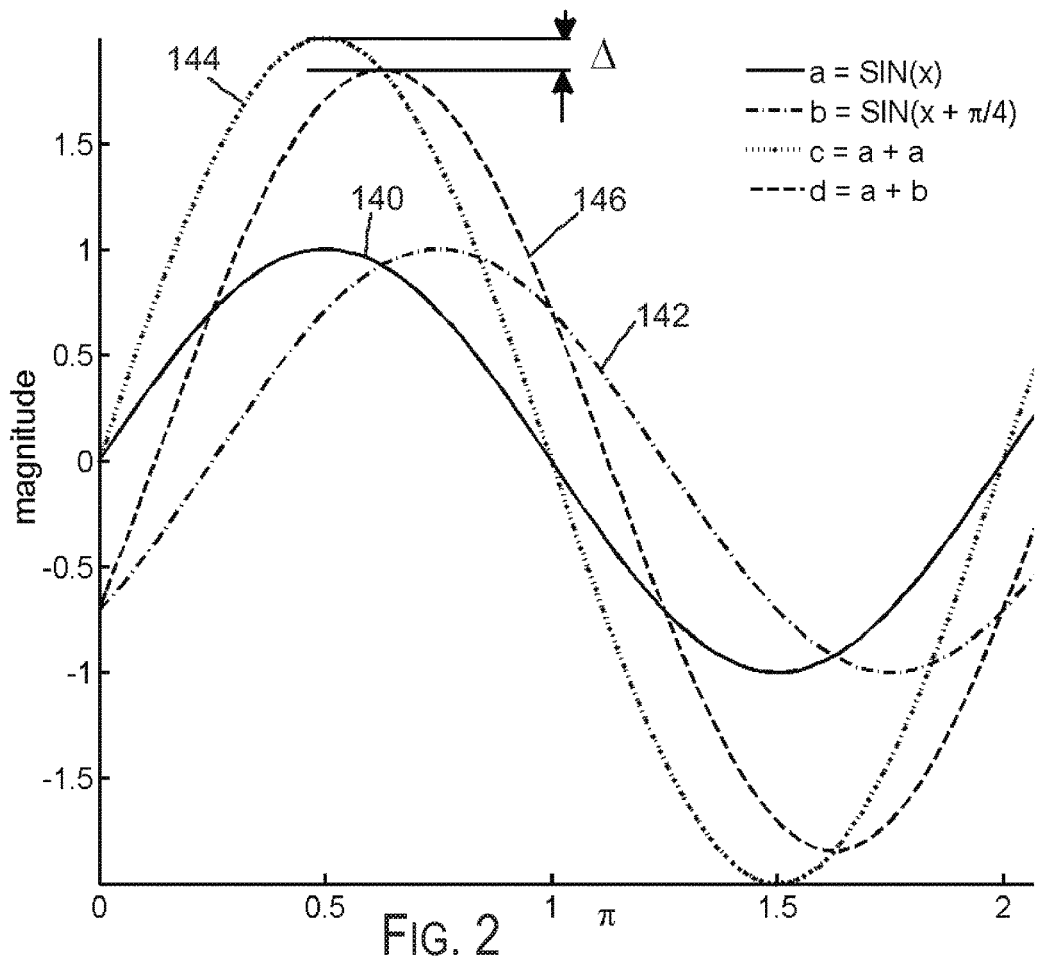
FIG. 2 is a plot of beamformer channel phase error example.

The Whittaker—Nyquist—Kotelnikov—Shannon sampling theorem establishes sampling condition for perfect signal restoration. However, the beamforming step is not dealing with signal restoration as such, but with the summation of discrete samples with delays subtracted to compensate the signal path differences in different channels where the error in producing perfect focusing delay compensation inversely relate to the beamformer sampling rate. To illustrate this in principle, FIG. 2 shows a situation where input signal 140 from one beamformer channel can be summed with its perfectly delayed (i.e. perfectly aligned) copy to produce a perfect beamforming output signal 144. However, if the sampling rate gives a phase error$+/-\pi/4$ (for instance if the system samples a 10 MHz signal with 40 MHz sampling rate) the sum of such input signal 142 from the second channel and signal 140 would produce an imperfect summation 146 with lower output signal magnitude. In order to maximize the signal-to-noise ratio of beamformer output signal it is desirable to keep sampling rate high to minimize this phase alignment error of focusing delays. However, using ADC with much higher sampling rates would drive the cost and complexity of a beamformer channel further up. Thus, the maximum allowable phase error (MAPE) criterion can be used as a design constraint to optimize the cost and performance of the beamformer.

In summary, the ultrasound signal returned from shallow depth would have largest bandwidth, thus, in order to keep MAPE small for the highest frequencies in the bandwidth the system needs to sample it at highest available sampling rate. On the other hand, signal returned from largest depth of scanning will have smallest bandwidth since its high frequency components will be removed by the attenuation, thus, the sampling rate can be safely decreased while maintaining the same phase error level. Such optimization of sampling rate and aperture has reciprocal relationship, thus the system can dynamically trade one for another while it captures and beamforms the signals.

Beamformer With Variable Aperture and Sampling Rate

Based on abovementioned principles or postulates, the preferred embodiment of the new ultrasound beamformer would start by sending an ultrasound pulse or train of pulses into the media and begin signal acquisition with a small aperture and high channel sampling rate. Then, as the interrogating ultrasound pulse propagates deeper, the aperture expands in size by gradual addition of arrays elements to its edges and the channel sampling rate would correspondingly drop, such that at some depth the beamformer has maximum aperture (maximum number of channels) and smallest channel sampling rate, defined as ADC sampling rate divided by the number of channels connected to ADC and form the current aperture.

Figure 3:
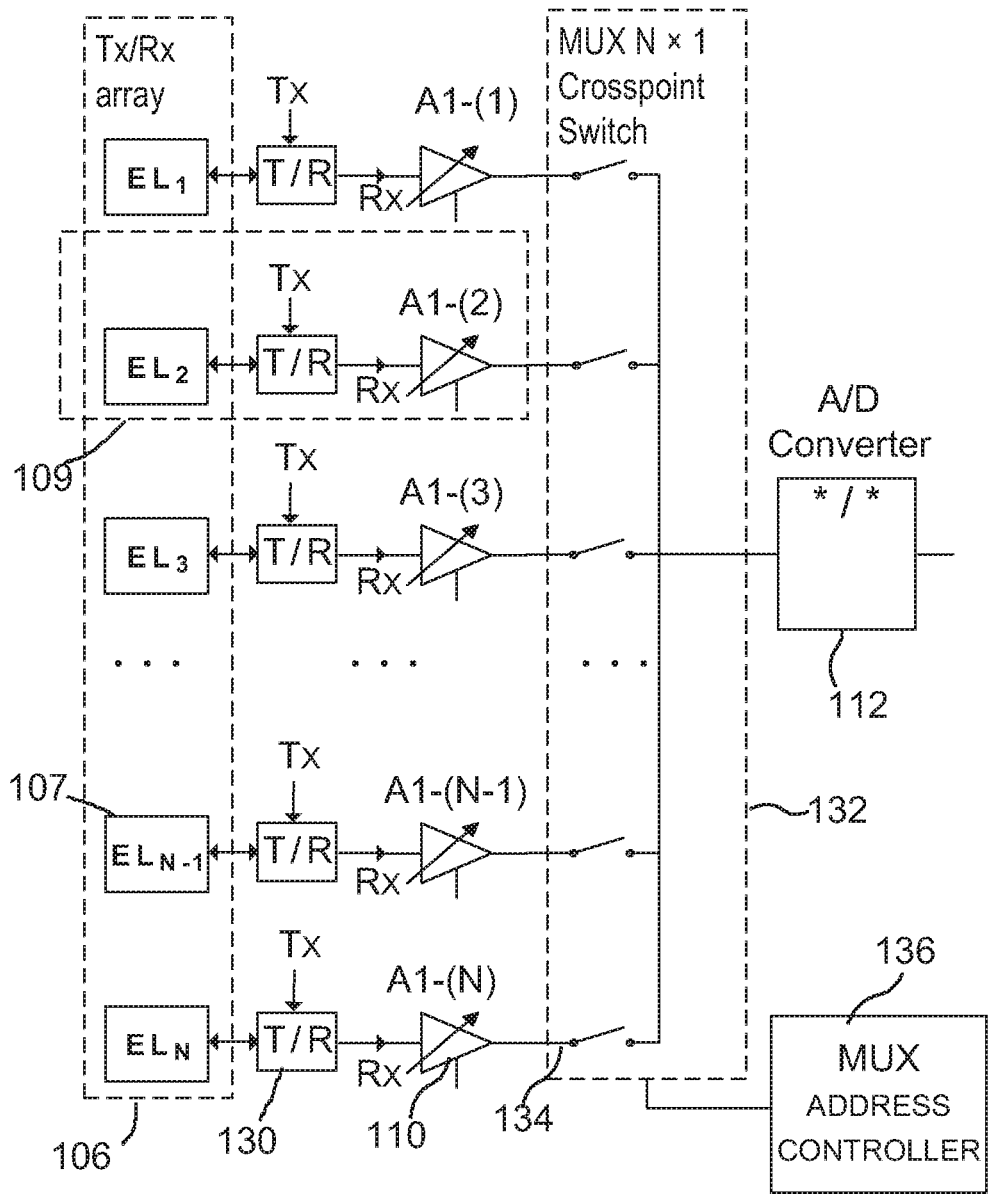
FIG. 3 is a schematic representation of a reconfigurable digital ultrasonic beamformer in accordance with one embodiment of the present invention.

FIG. 3 shows a simplified illustration of such a receive beamformer architecture. Each receive channel may consist of piezo-element 107, transmit-receive (T/R) switch 130 and signal conditioning block 110 consisting of a combination of filters, linear and voltage controlled amplifiers (VCA) connected to N×1 multiplexor MUX 132. The MUX 132 connects one or several beamformer channels 109 via switches 134 selected by MUX address controller (MUX-AC) 136 to the input of a high speed ADC 112. The output of ADC 112 is a digitized sample 122 that typically stored for further processing as generally known in the art.

Alternatively, signal conditioning block 110 may include a sample-hold or track-and-hold circuitry, or such circuit can be included into MUX 132 schematic. Switches 134 may be implemented as semiconductor switches, or MEMs, or any other suitable technology that allows for fast and reliable switching.

The MUX-AC 136 selects the group of elements to serve as a current aperture and sequentially connects them with the ADC input, such that the signal from each element in the current aperture is continuously sampled with proper sampling rate (e.g. if ADC works at 600 MSPS and it sequentially acquires data from 15 elements, then each element is sampled at 40 MSPS). The maximum number of element connected to one ADC can be calculated as $N=f_{ADC}/f_S$, where $f_{ADC}$ is the maximum ADC clock speed and $f_S$ is the sampling rate of an individual channel. MUX address controller 136 can dynamically connect one selected channel to ADC 112 (for instance address 000010000 connect middle element in the aperture to ADC 112) or can connect several arbitrarily chosen channels by directly setting address with (0110111111000) or by using second layer of channel switches.

Figure 4:
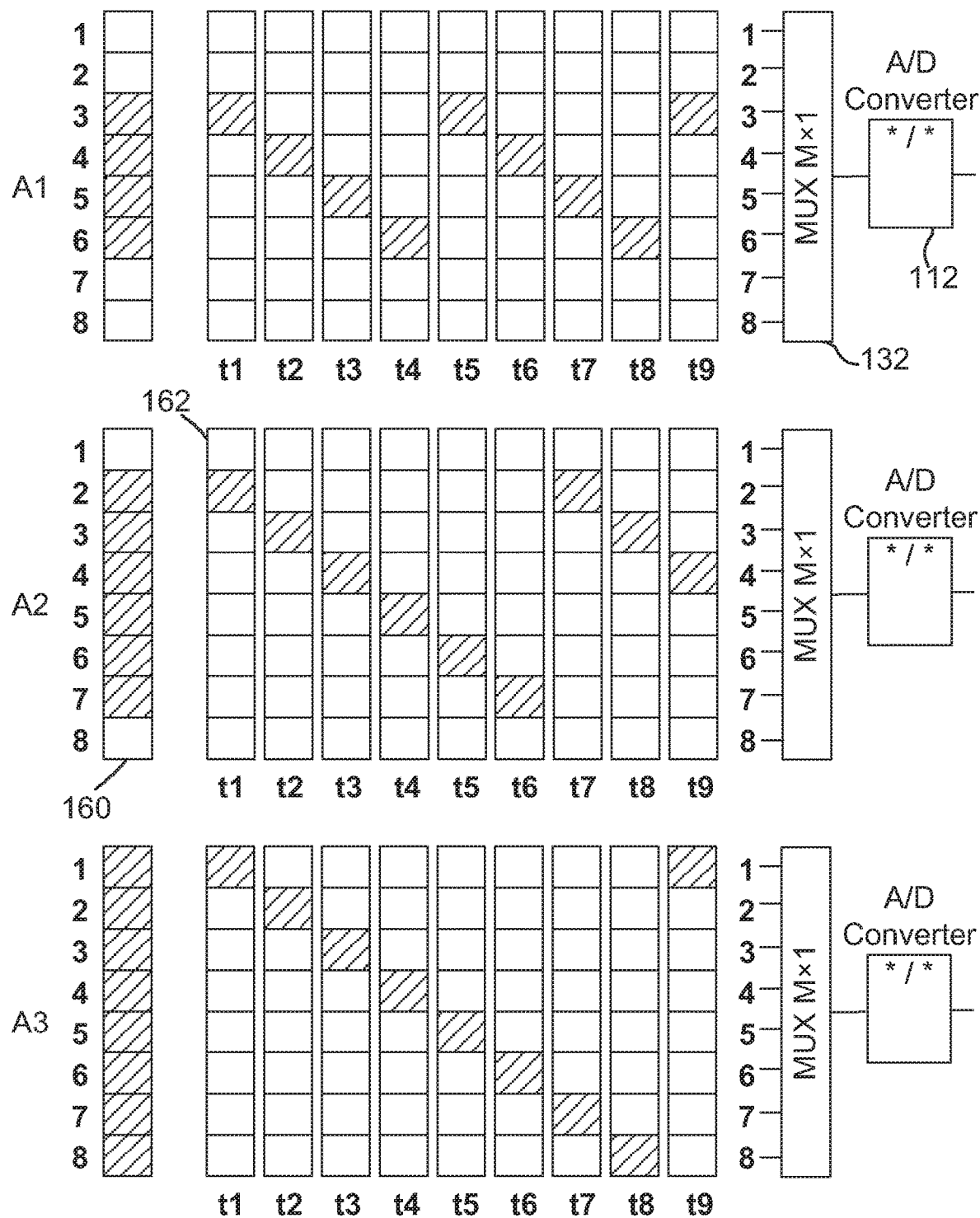
FIG. 4 is a schematic representation of different apertures and corresponding timing diagrams illustrating work of the ultrasonic beamformer according to the present invention.

FIG. 4 illustrate the working of such a beamformer showing three sequential apertures $A_1$-$A_3$ for a simple 8 elements array 160. Column 162 in the diagram shows which element of array is connected to the ADC 112 at sample time $t_i$ as a shaded box. In this example, aperture $A_1$ is used at some shallow depth and at time $t_1$ MUX-AC 132 connects element 3 to ADC 112. At every clock $t_1, t_2, \ldots t_N$, one element of the active aperture is connected through MUX 132 to the ADC 112 and a sample is acquired. ADC would sample each element in the current active aperture continuously in circular fashion cycling through clock times $t_1, t_2, \ldots t_N$ until the current aperture changes to different one. The channel sampling rate in this situation will be $f_S=f_{ADC}/4$ (if setting $f_{ADC}=240$ MHz, $f_S=60$ MHz). Then, when ultrasound signal reaches a certain depth, aperture expands to $A_2$ with six elements in it and channels sampling rate drops, correspondingly, to $f_{ADC}/6$ or 40 MHz, then at larger depth aperture becomes A3 and channel sampling rate $f_{ADC}/8$ or 30 MHz while sampling rate of ADC 112 remains constant at 600 MHz in our example.

The MUX address controller 136 role is to select the current aperture from all the elements of array, form and dynamically update the address of the beamformer's channel currently connected to the ADC 112 such that at every clock $f_S$ one or plurality of beamforming channels can be connected to the ADC 112. The addressing can be done programmatically in software, firmware or in hardware by look-up-tables or being calculated dynamically using a suitable algorithm that is well understood to those practicing in this art.

Figure 5:
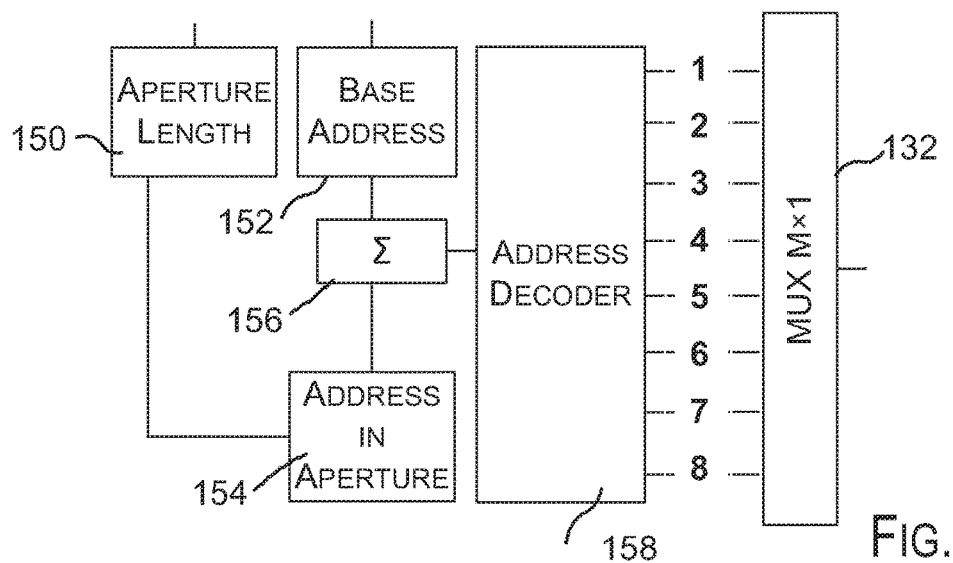
FIG. 5 is a schematic representation of an embodiment of the MUX address controller for use in a reconfigurable digital ultrasonic beamformer in accordance with one embodiment of the present invention.

One possible realization of the MUX-AC 136 is shown on the schematic diagram on FIG. 5. The multiplexor address controller includes three registers: Base Address Register 152 that stores the address of the element at the beginning of the current aperture, Aperture Length Register (ALR) 150 that holds the number of elements in the current aperture and Address in Aperture Register 154 holding the element's number that is connected to ADC during the current clock cycle. This number increments at every clock cycle from zero to number stored by register 150 and then resets back to zero, or it can also work other way around counting down from ALR value to zero, and resetting to the ALR value. The address of currently selected element of array is found by summing in the block 156 the base address 152 and the address of currently selected element in aperture.

Figure 6:
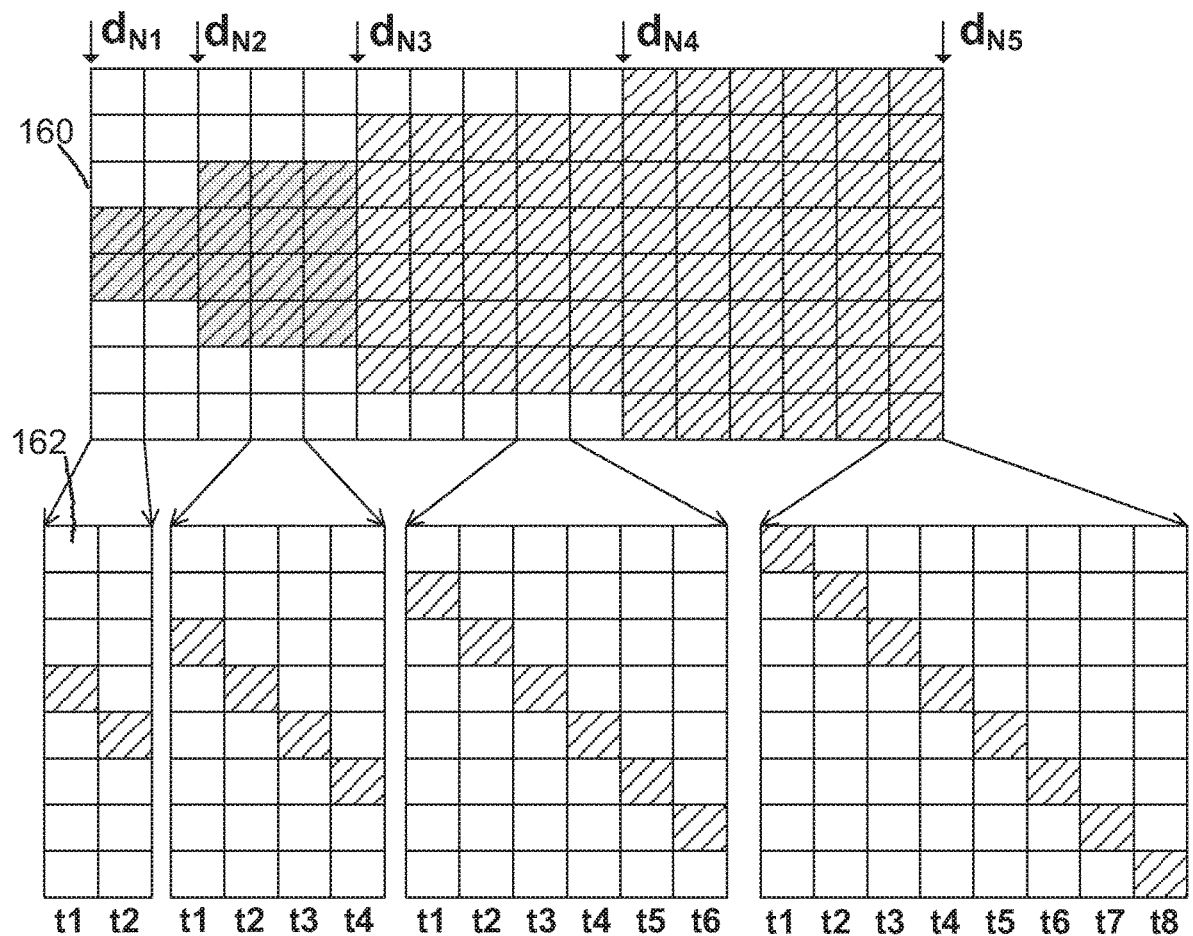
FIG. 6 is a schematic representation of aperture change with depth of the return signal and corresponding timing diagrams illustrating work of the ultrasonic beamformer of the present invention.

The values of the base address and address in the aperture are summed in block 156 every clock cycle and this continuously updated address through the address decoder 158 is connected to the MUX's 132 control inputs to define which channel 109 is connected to the ADC 112 input at every given clock time as it is shown in FIG. 4. Other methods may have arbitrary address set to the address decoder directly at every clock cycle allowing arbitrary number of channels to join or an arbitrary channel being selected every clock cycle for the purpose of realization of some specific beamforming algorithm. FIG. 6 illustrate schematically how active aperture and sampling rates may change with depth of the return signal, where depth values $d_N$ can be taken from the Table 1. As before, the figure shows the active aperture and currently selected aperture channel as shaded squares and sampling times within the sampling cycle as $t_i$.

Figure 7:
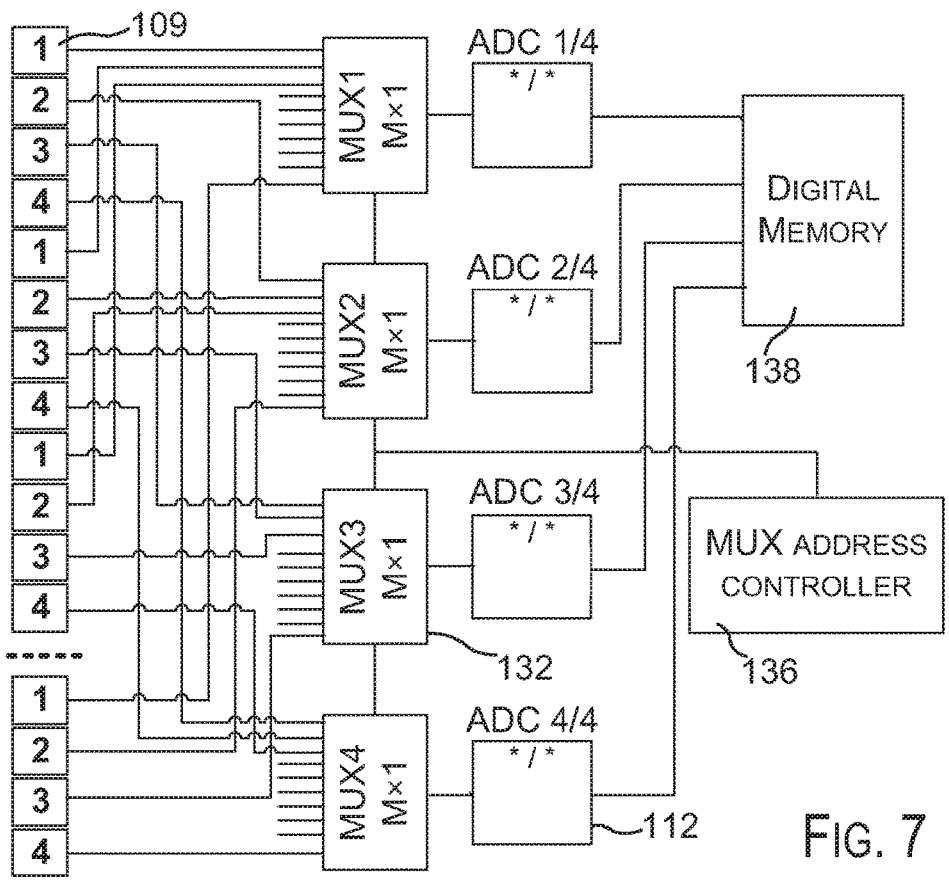
FIG. 7 is a schematic representation of an embodiment of the reconfigurable digital ultrasonic beamformer with expanded aperture and multiple ADC channels in accordance with one embodiment of the present invention.

FIG. 7 schematically demonstrate how this technology can be combined into a bigger aperture. This example shows four MUX and ADCs, each working with a plurality of beamforming channels. In the figure, beamforming channels 109 are labeled by the number of MUX to which it is connected. Demonstrating the advantages of this architecture, is the use of an existing Texas Instrument ADS4449 Quad-channel, 14-bit, 250-MSPS A/D converter as a base for the design. Then, the system can have a maximum of 16 beamforming channels 109 connected to each MUX 132 to a total active aperture of 64 channels.

Table 1 shows an example how the size of the aperture and the sampling rate of a channel could change with depth. Obviously, the present invention encompasses the selection any other arrangement of sample rates, channel number and depth.

TABLE 1

| Starting Depth $d_N$ [cm] | Sampling rate per channel fs [MSPS] | N of elements in one ADC channel | N of elements in four ADC channel |
|---|---|---|---|
| 0 | 120 | 2 | 8 |
| 2 | 80 | 3 | 12 |
| 4 | 60 | 4 | 16 |
| 6 | 48 | 5 | 20 |
| 8 | 40 | 6 | 24 |
| 11 | 30 | 8 | 32 |
| 14 | 24 | 10 | 40 |
| 17 | 20 | 12 | 48 |
| 20 | 15 | 16 | 64 |

Standard design, would require 64 ADCs to cover 64 channels aperture, or depending on the desired sample rate, from eight (×8 channels ADC chip) to sixteen chips with ×4 ADCs with corresponding increase in power consumption and circuit board size which is a significant load for any portable battery operated device. If the present system is limited to beams symmetrical in relation to the central element (no beam steering in azimuthal direction), then each channel described above can be connected to two elements symmetrically (first element+last element in the aperture, second element+penultimate element, etc.) and the system aperture can be doubled in size. In other words if the beam formed by the beamforming system and method is symmetrical about at least one central array element then the channels forming the aperture (other than the channel including the at least one central array elements) are each formed of a plurality of elements symmetrically spaced about the central array element(s). This "elements joining" can be accomplished by usual means known in art, for instance, referring to FIG. 13A, by inserting another analog multiplexor to switch outputs of MUX 132 and inputs and ADC 112 such that few programmatically selected MUX 132 can be connected to any of ADC 112 inputs. Then, using the example in the Table 1, the system can beamform full 128 elements array with just four ADC or 32 times gain as compared to the standard digital beamforming architecture.

In the preferred embodiment of this beamformer digital output of AD converters 112 is stored in a digital memory. There, data coming from ADCs 112 outputs are separated into channel data. Prior to performing beamforming calculation channel data can be up-sampled to the highest sampling rate of the ADC and blanks spaces between samples filled by interpolation, then passed to beamforming algorithm for calculation of the beamforming output.

In another embodiment or variation of the present invention, channel data can be interpolated to any sampling frequency chosen by the beamforming algorithm.

In another embodiment or variation of the present invention, channel data can be interpolated to any number of different sampling frequencies chosen by the beamforming algorithm and results combined with any chosen set of time, spatial or spectral filters to produce the beamformed output.

In another embodiment of this invention, the depth boundaries between regions with different sampling rates can be variable as in line interlacing principle—odd and even lines would have different boundaries shifted up and down, then information from neighboring lines is used to fill the voids in the transition zone.

In another embodiment of this invention the beamformer digital output of AD converters 112 is stored in a circular digital buffer holding data volume needed to perform beamforming on the channel data, such as delay-sum operation, and the system discards old data not required for future beamforming calculations.

In the preferred embodiment of this beamformer Doppler data are acquired with a single sampling speed.

Method to Grow Active Aperture Faster

Figure 8A:
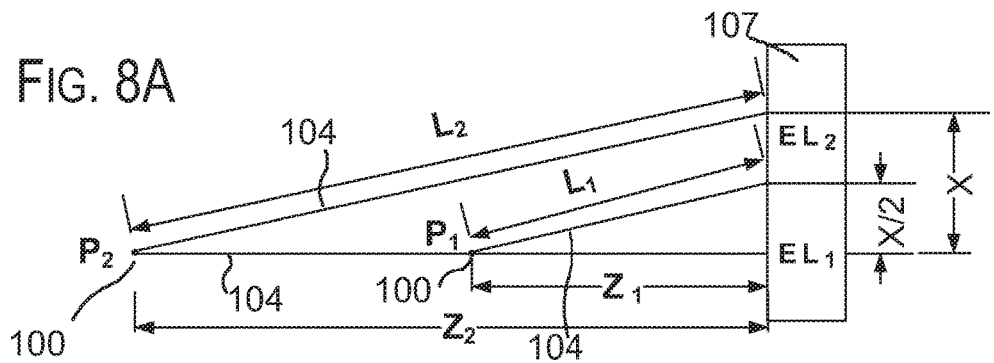
FIGS. 8A and 8B are plots of basic geometry explaining the signal return paths and associated delays a in receive beamformer channel 109 in accordance with the present invention.

Another embodiment of this invention can be used to grow the active aperture faster with depth while preserving the sampling rate of the beamformer and keeping travel time delay errors small at the same time. Referring to the FIG. 8A, where 107 is an array element, 100 is the scattering point and 104 is travel path, due to the finite dimensions of the array element, there will be a difference in travel times from the point in space $P_1$ to the center of the element 107 and to its edge as:

$$\Delta t_1 = \frac{L_1 - Z_1}{c} = \frac{\sqrt{\frac{x^2}{2} + Z_1^2} - Z_1}{c}$$

where c—is the speed of sound in the media and x—is the distance between the centers of two neighboring elements or element's pitch. As the depth increases, this $\Delta t$ goes from x/2c to zero for the elements lying close to the beam axis. Thus, every element in array has an inherent phase error arising from path difference between edges of the element and its center and the magnitude of this phase error depends on the element size and the signal frequency. For elements lying near the beam axis, this error is small. For example, a generic curved probe C5-2 with elements' pitch x=0.476 mm and point $P_1$ being at 10 mm depth, will have error $\Delta t_1 \approx 1.86$ ns which smaller indeed as compared with 5 MHz±π/16 maximum allowable phase error $\Delta t \approx 6.25$ ns.

Remembering that this phase error decreases with distance, we can find, for example, that the phase error for the point P2 (referring to the FIG. 8A) being at 40 mm depth and having element size 2·x will be the same $\Delta t \approx 1.86$ n as for the element size x and point $P_1$ being at 10 mm depth.

$$\Delta t_1 = \Delta t_2$$

$$\frac{L_1 - Z_1}{c} = \frac{L_2 - Z_2}{c}$$

$$\frac{\sqrt{\frac{x^2}{2} + Z_1^2} - Z_1}{c} = \frac{\sqrt{x^2 + Z_2^2} - Z_2}{c}$$

Thus, at the depth $P_2$ the system can simply sum contributions from two neighboring elements or putting it in more general form—the system can grow our aperture with depth by simply joining (or summing) the neighboring elements. As the signal return depth increases, more elements can be added to the "central" element without introducing additional phase error. This aperture expansion describes the situation for the elements lying close to the axis of the beam.

Figure 8B:
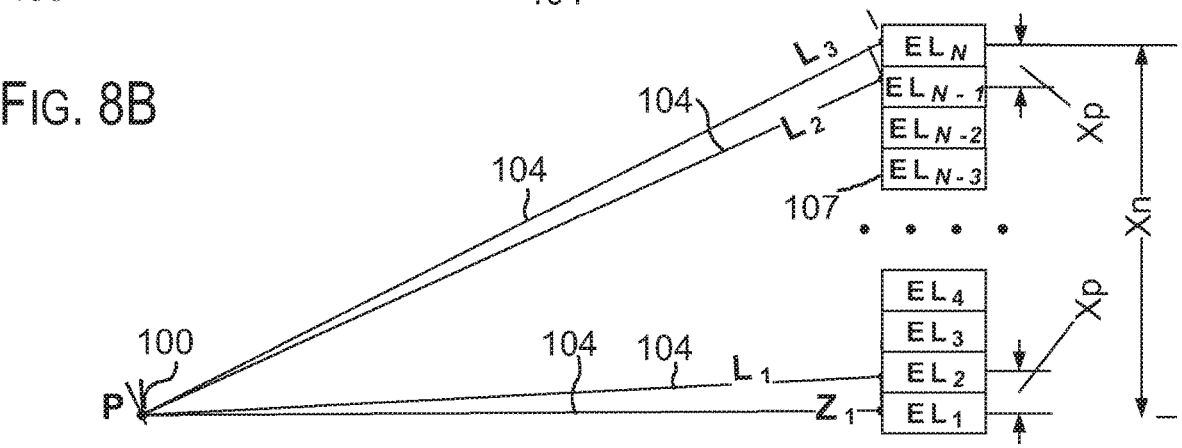
Figure 9:
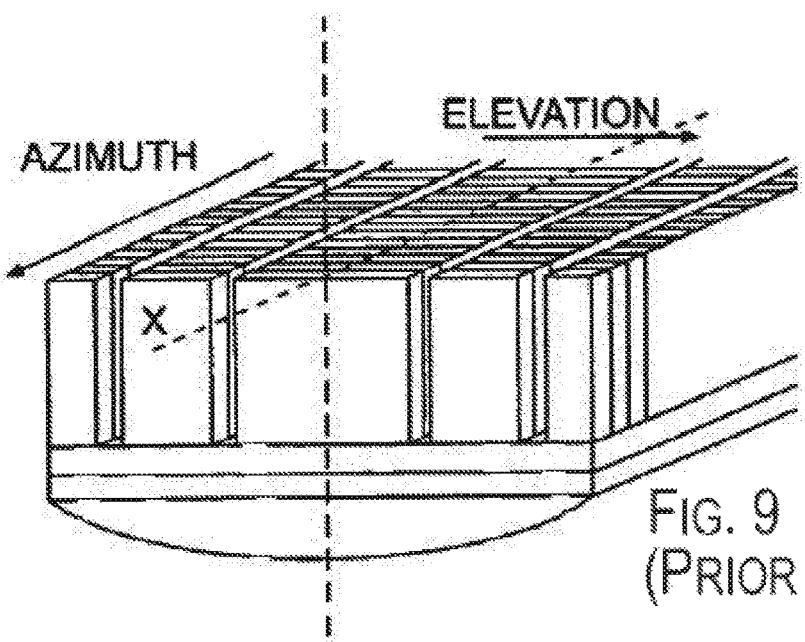
FIG. 9 schematically illustrates the element dimensioning in a known 1.5D array.

For the elements lying closer to the edge of the aperture the situation is different. As it can be seen from the drawing on the FIG. 8B, the arrival time differences for the center and the edge of an element lying away from the beam axis can be a lot bigger than $\Delta t$ of "central" elements of the aperture for linear arrays and even bigger for the curved arrays. Using the same example of an element with pitch x=0.476 mm being at $x_n$=20 mm from the beam axis and point P=100 mm, there is an error in arrival times from pulse pressure wavelets coming to the edge and to the center of the element $\Delta t \approx 61.7$ ns, thus, even at large depth, the element's internal phase error is large relative to the errors of more "central" elements. Therefore, moving from the center of the aperture to the edge, the size of the composite elements ("composite elements" being defined as neighboring elements directly connected or summed to one another) must become smaller. The way 1.5D array typically split elements in elevational direction gives a good example illustrating this situation. In it, the biggest size in elevational direction have the central elements, and the sizes of the elements away from the central line decrease in inverse proportion to its distance to the central line (as it is shown on FIG. 9 extracted from U.S. Pat. No. 6,656,124 entitled "Stack based multidimensional ultrasonic transducer array"). Such element splitting can be seen as an embodiment of a Fresnel focusing, known in optics. Thus, this method of growing aperture can be called a dynamic Fresnel beamforming.

Figure 12:
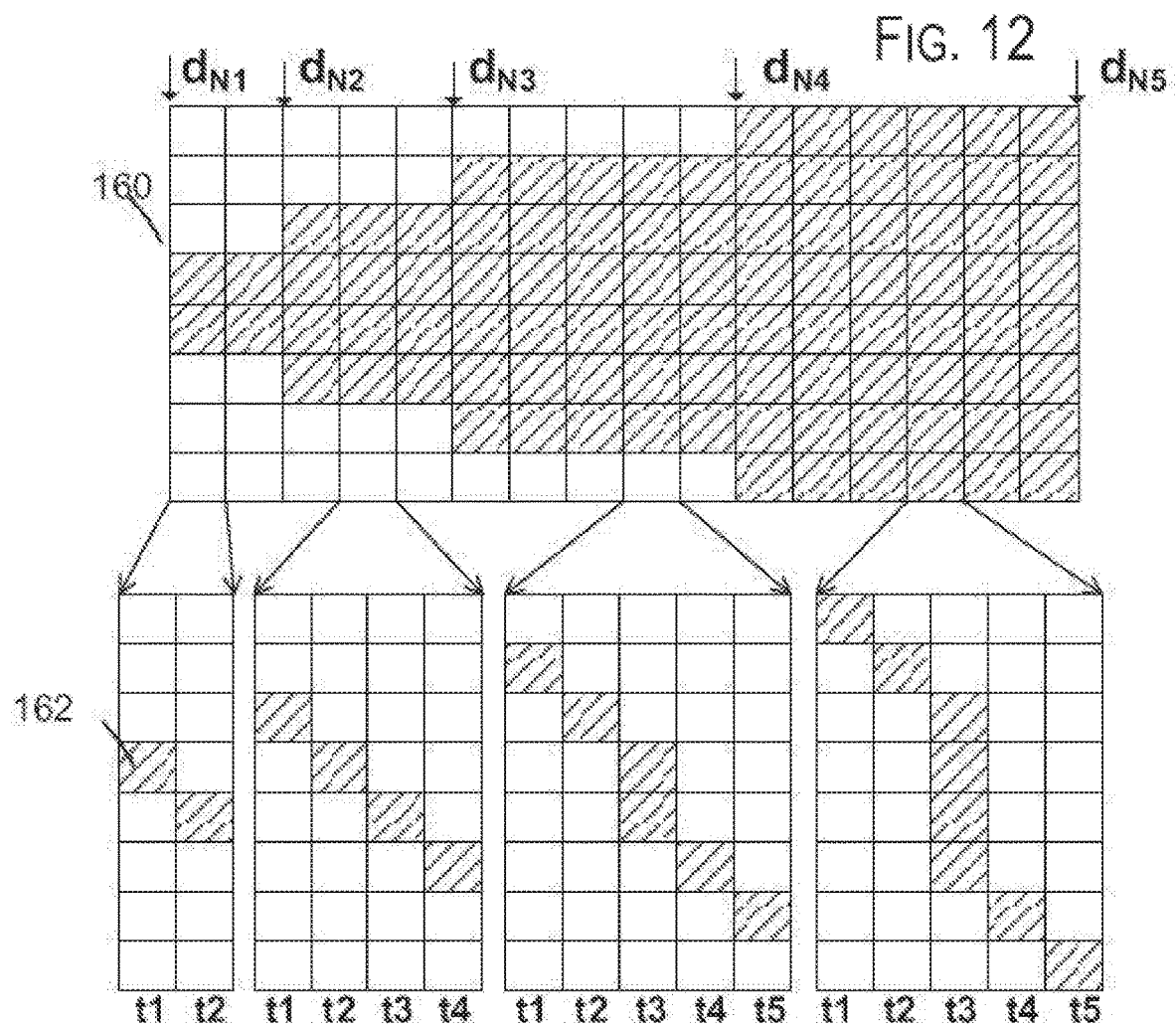
FIG. 12 is a schematic representation of aperture change with depth of the return signal and corresponding timing diagrams illustrating work of the ultrasonic beamformer of the present invention.
Figure 10:
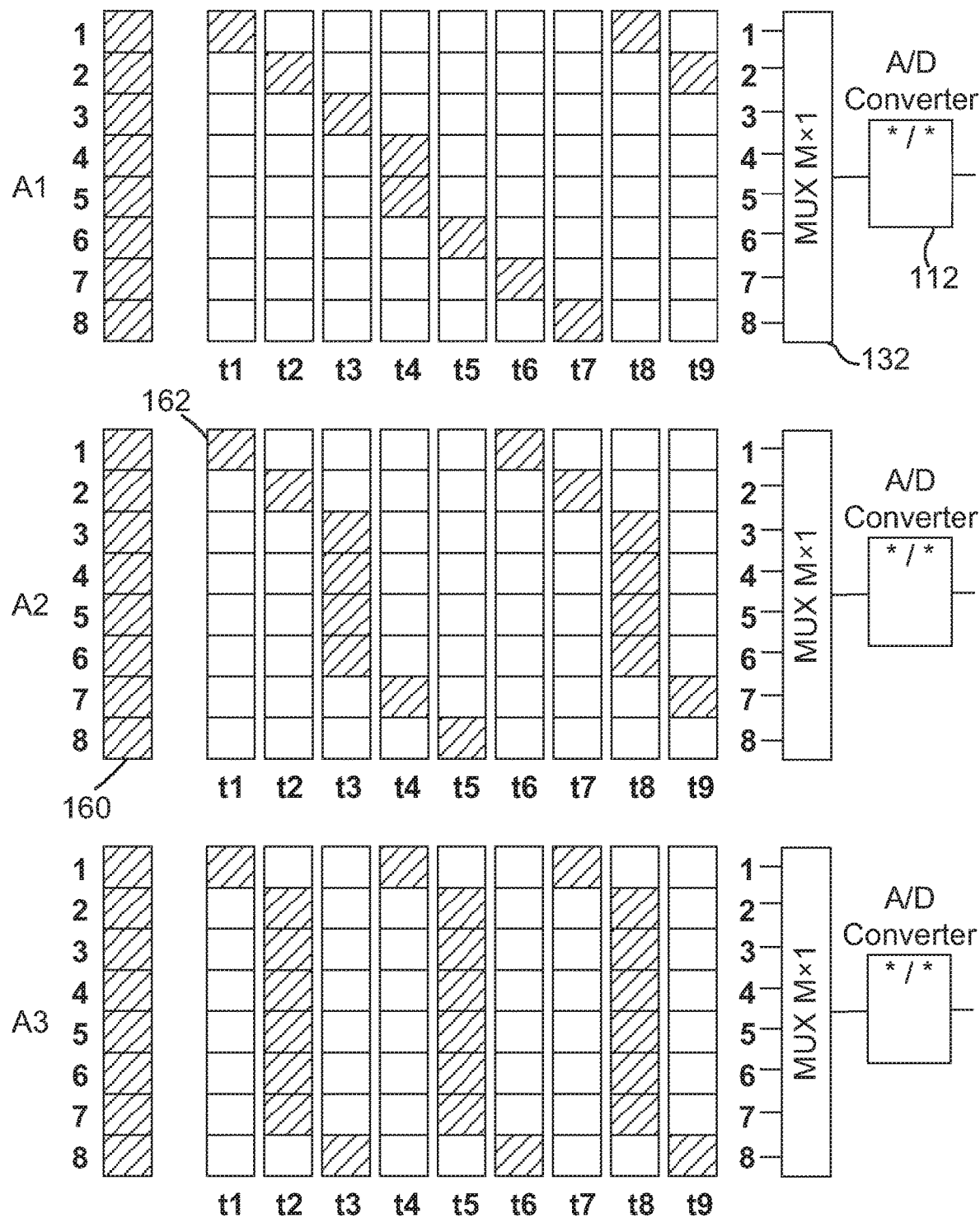
FIG. 10 is a schematic representation of different aperture compositions and corresponding timing diagrams illustrating work of the ultrasonic beamformer of the present invention.
Figure 11A:
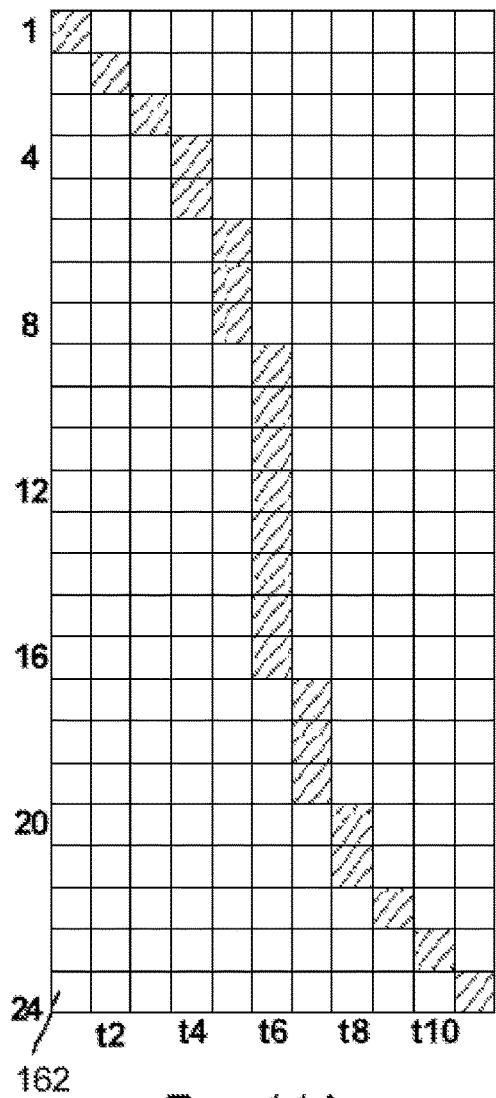
FIGS. 11A, 11B, 11C schematically illustrate examples of larger apertures with "composite" elements and corresponding timing diagrams illustrating work of the ultrasonic beamformer of the present invention.
Figure 11B:
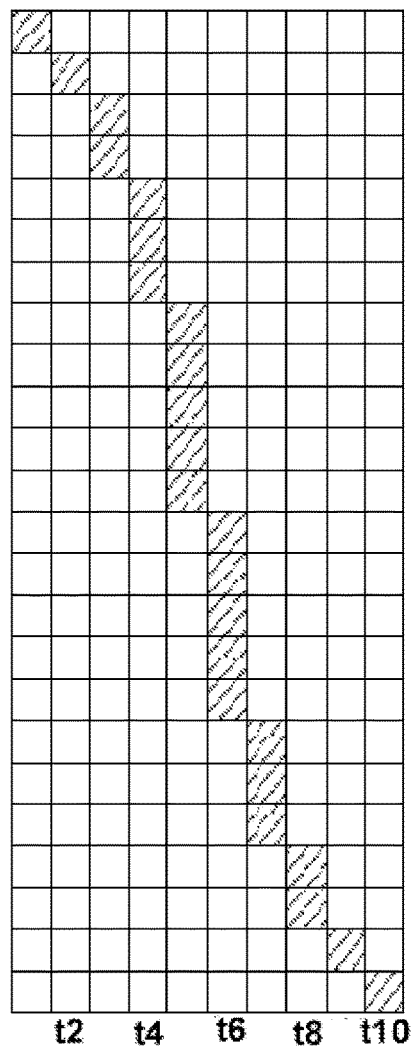
Figure 11C:
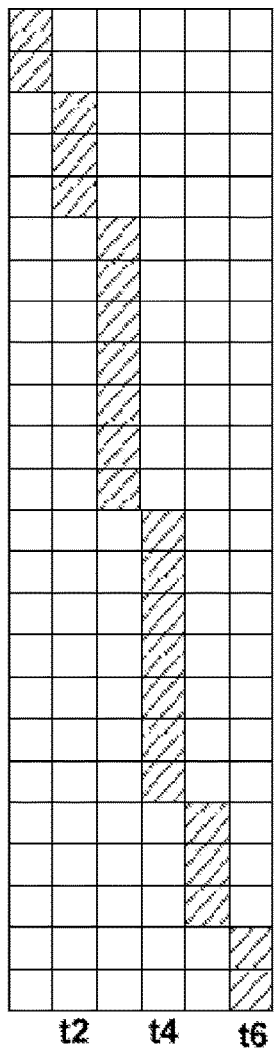

This invention allows dynamically control aperture position, size as well as size of "composite elements" in the aperture to optimize both beamforming channels sampling time with depth. FIG. 10 shows three examples how the same 8 elements aperture could be sampled in the system of the present invention, giving three different sampling rates: $f_S=f_{ADC}/7$ for aperture $A_1$, $f_{ADC}/5$ for aperture $A_2$, and $f_{ADC}/3$ for aperture $A_3$, where $f_{ADC}$—is the sampling rate of the ADC 112. FIG. 11 give three examples how, bigger 24 elements aperture, could be implemented in the system of the present invention with $f_{ADC}/11$, $f_{ADC}/10$ and $f_{ADC}/6$ sampling rates and FIG. 12 gives example how aperture can expand with depth while preserving its sampling rate in the system of the present invention.

Figure 13A:
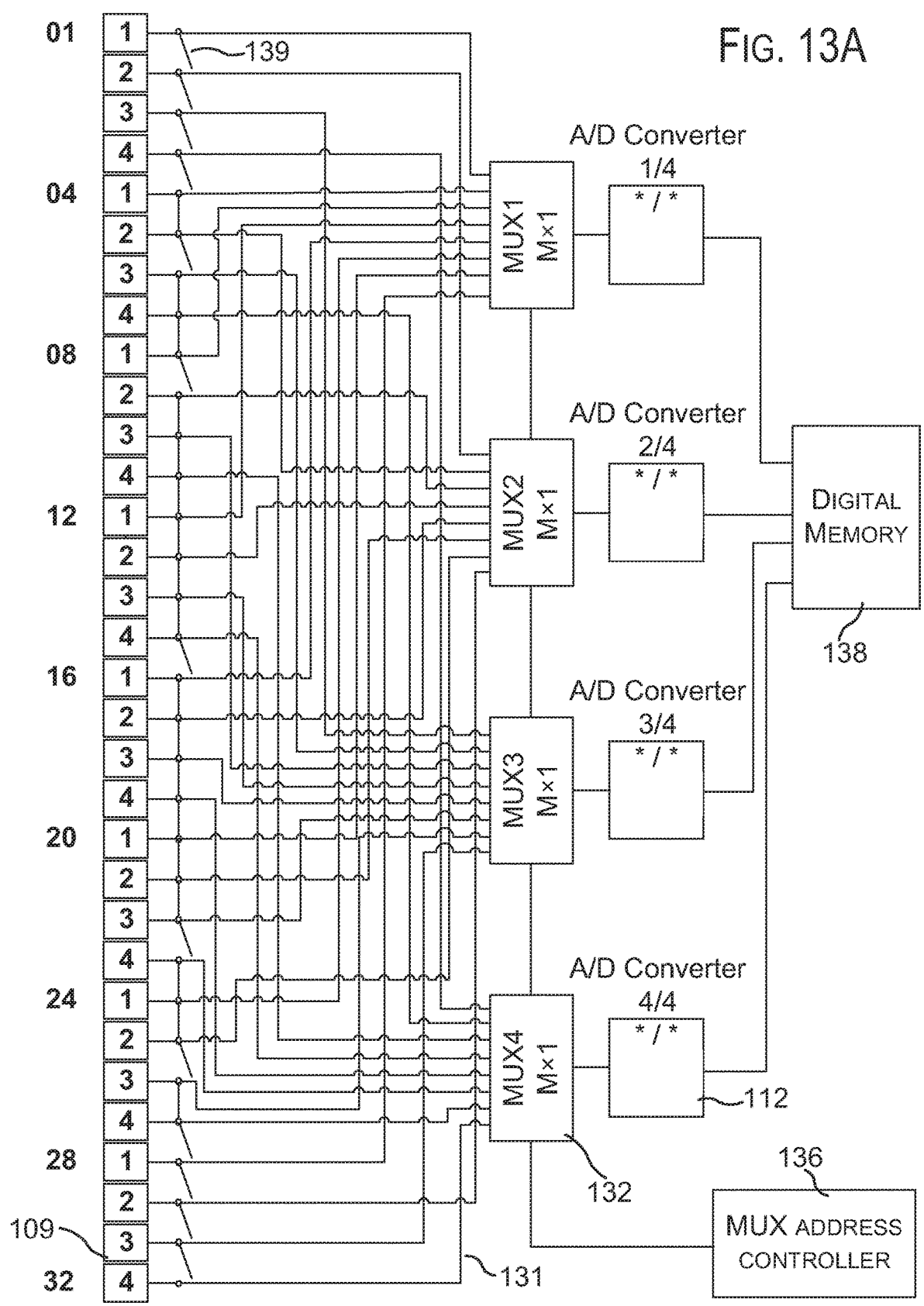
FIGS. 13A and 13B are schematic representations of a reconfigurable digital ultrasonic beamformer in accordance with one embodiment of the present invention.
Figure 13B:
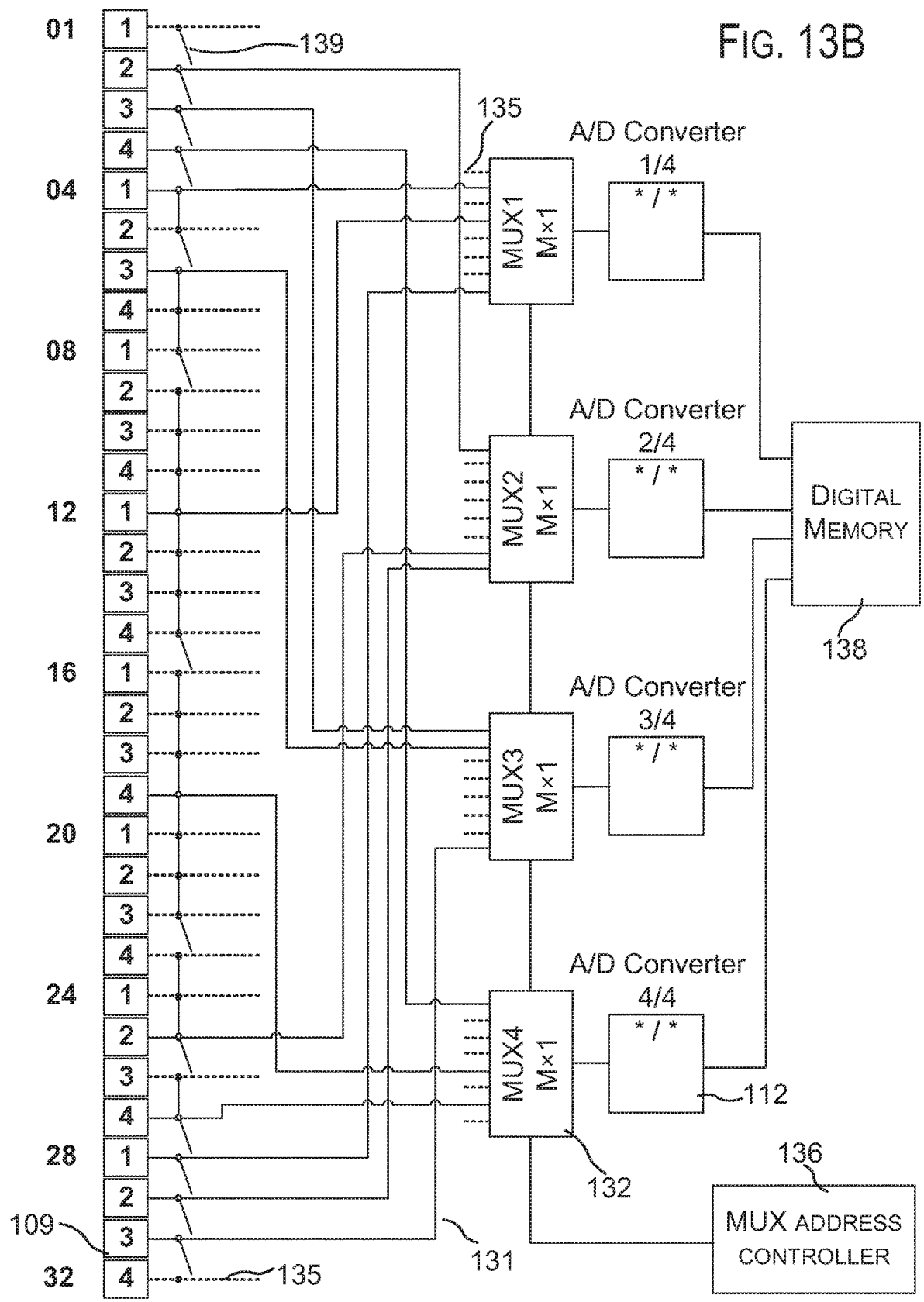

As it was stated above, such aperture control can be implemented by directly supplying addresses to the MUX 132 that would connect one or few neighboring channels 109 to the input of corresponding ADC 112, or (referring to the FIG. 13A) it can be done for instance by introducing another layer of switches 139 in front of MUX 132 (or in front of elements 107 or anywhere in the channel 109 space that is deemed fit by the art) that could connect outputs of channels 109 in parallel if required. FIG. 13 shows another example of implementation of 32 channels beamformer with FIG. 13B giving an example of 30 elements aperture configured as 1-1-1-2-3-7-7-3-2-1-1-1 aperture where number shows how many element or channels are combined in the "composite" elements of this aperture. In this representation solid lines 131 shows the "live" connections and dotted lines 135 connections that being "skipped" by the multiplexors 132. The sample rate in this example is $f_{ADC}/3$, or if we use the same realistic example of ADC chip as above, this 30 elements aperture is sampled at 240/3=80 MSPS (Mega samples per second) using only four ADCs while, in contrast, a standard digital beamformer would need 30 such ADCs with corresponding rises in board space, consumed power and heat generation almost 8 times over proposed design of the present invention.

In another embodiment of this design, switches 139 together in whole or partially with circuitry constituting MUX 132 and MUX control 136 can be moved into the probe array handle to sit next to the array 106. In this embodiment, a new design for the array head is presented that would allow dynamically controlling the azimuthal, or elevational, or both dimensions of the array elements to minimize the number of beamforming channels and wires in the probe cable while preserving the image quality of data.

In another embodiment, the array's elements can be made sufficiently small to allow phased array operation and to have elements edge-to-center phase error small even at the edges of aperture and outputs of such elements could be joined by switches 139 to allow dynamic control of the aperture size with depth by manipulating the sizes of such "composite elements". Such variable pitch array can be used independently or in any combination with existing beamforming architectures—analog, digital, analog random access memory ARAM beamformers.

In another embodiment, the array's elements can be made sufficiently small to allow phased array operation and to have elements edge-to-center phase error small even at the edges of aperture and outputs of channels 109 can be directly summed with MUX 132 either by a voltage or current adder, or on in a sample-hold cell, separate or a part of the ADC 112 circuitry by MUX address controller 136 directly setting addresses of all channels currently connected to ADC 112 in clock time $t_J$ as described above.

In another embodiment, the pitch or size of array's elements varies linearly with the elements position within the array, or changes in accordance to some smooth or step function of element's position within the array. For example, such an array can be designed having the pitch of the elements linearly decrease with distance from the array center.

Figure 14:
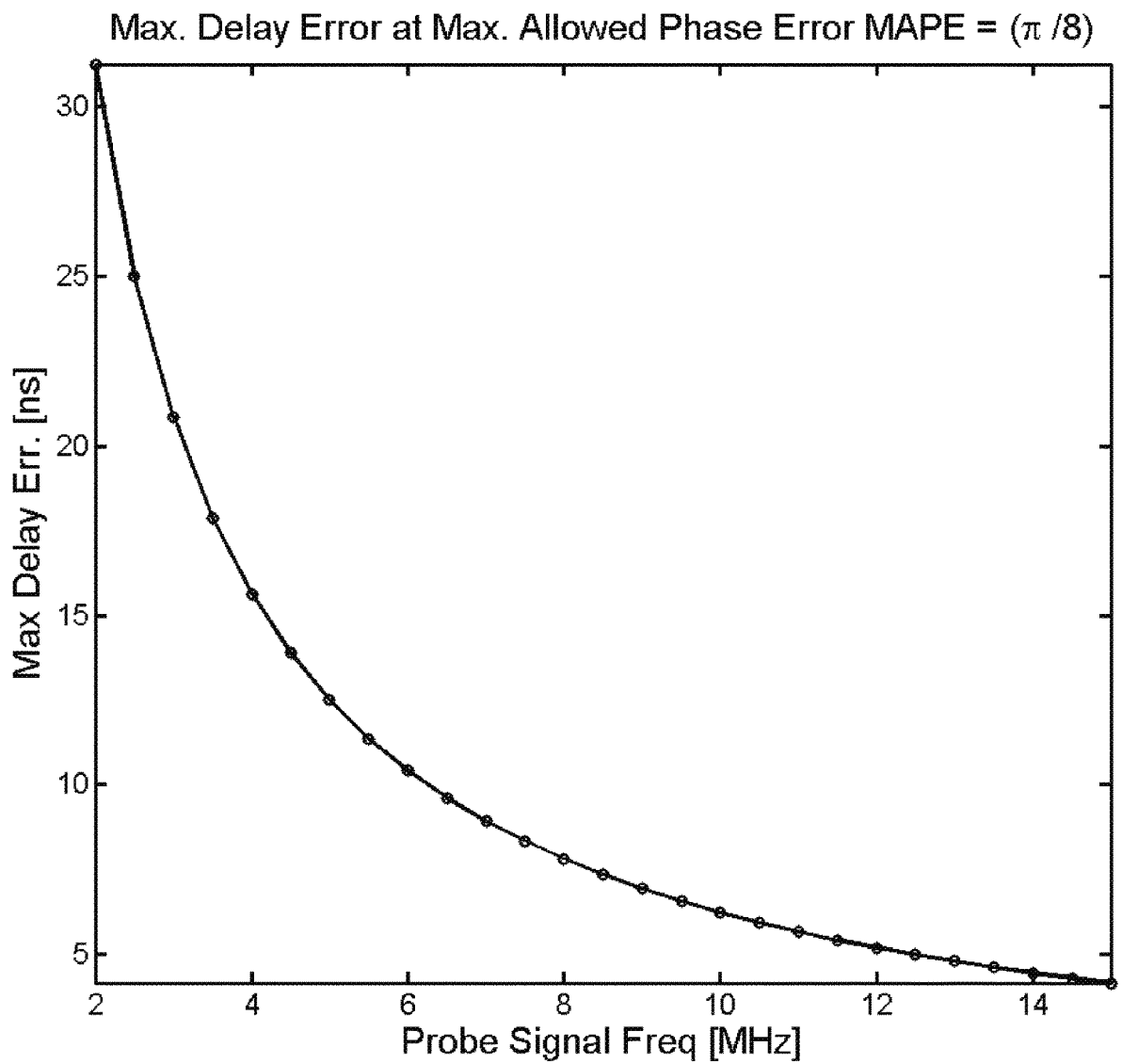
FIG. 14 is a plot of maximum allowed phase errors for different probe frequencies.
Figure 15:
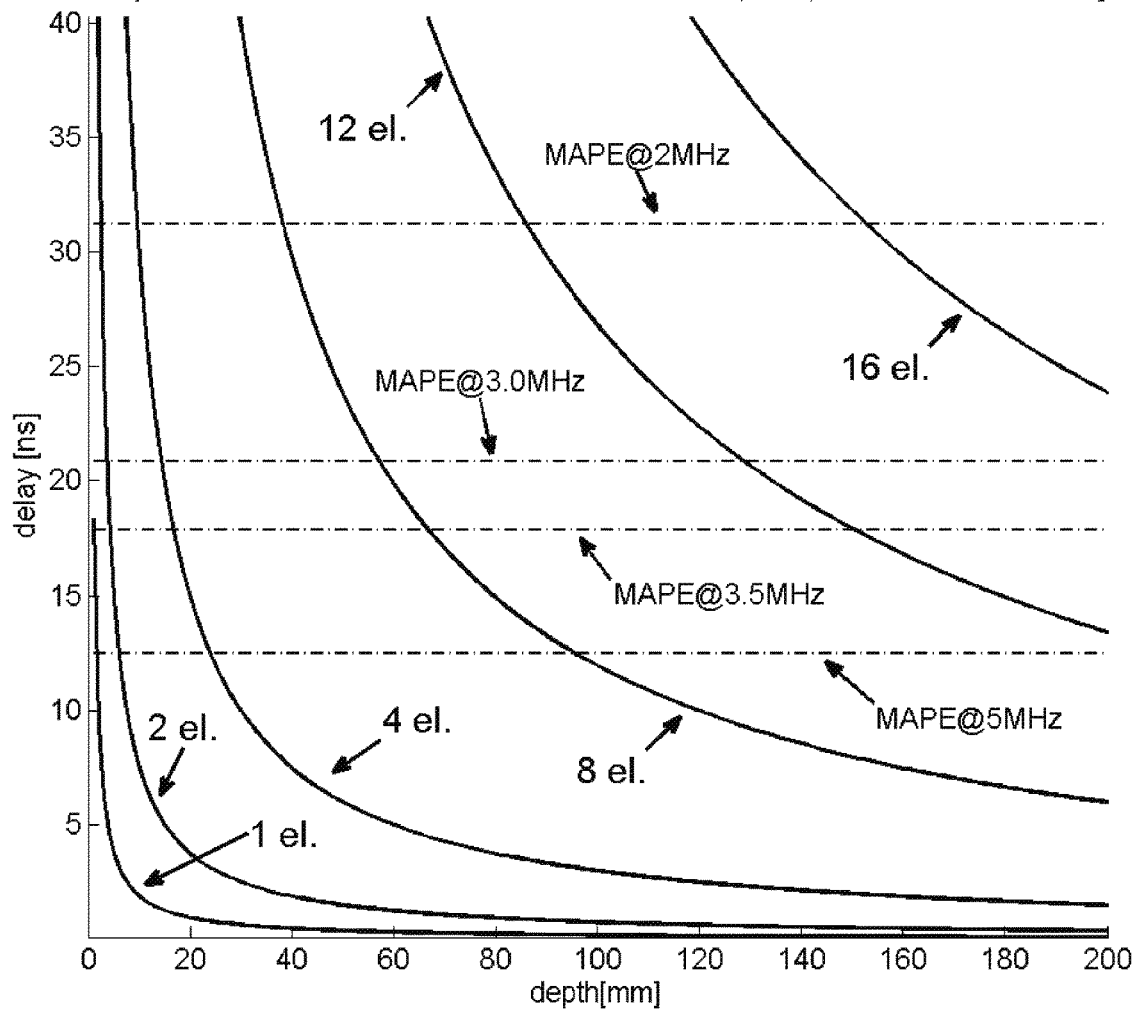
FIG. 15 is an example plot of maximum allowed composite element sizes as function of maximum phase errors for a receive beamformer channel in accordance with one aspect of the present invention.

The design criteria for the maximum allowed size of the composite element of the aperture as function of the depth, receive signal frequency bandwidth and element position in the aperture can be developed from the maximum allowed delay error values as it was briefly discussed above. Start by setting the maximum allowed phase error (MAPE) for the highest probe frequency which is expected to be captured at the depth. FIG. 14 show an example of a plot of maximum delay error as function of the signal frequency at MAPE=±π/16. Then, knowing the array elements pitch and position relative to the receive beam axis, it is possible to calculate distances at which elements could be summed directly together with error that can be neglected. FIG. 15 shows an example of such calculations for a generic curved C5-2 probe for elements close to the axis of the beam. There, shown on FIG. 15A, at 13 mm depth, even for 5 MHz frequency, directly sum phase error is much less than maximum allowed phase error for 5 MHz sampled at 80 MHz and at large depth, which would not expect to receive frequencies above 3 MHz, the system could directly sum up to 12 elements as one "composite element" in one ADC clock cycle.

In another embodiment, the array's elements constituting the current aperture can be combined into "composite elements" with asymmetric sizes when receive beam axis is directed on an angle to the surface of the probe, as in phased arrays. There, a composite element having a sharp angle with a beam axis in azimuthal direction could have more elements combined than a composite element lying on the other side from the central element of aperture and making the obtuse angle with the receive beam direction. Using the convention adopted for describing the FIG. 13B, elements of 32 element aperture could be configured as 1-1-1-2-4-8-7-3-2-1-1-1 where number shows how many element or channels are combined in the "composite" elements of this aperture and beam axis is inclined left in this example.

Unequal size of composite elements in each side of an aperture can be accommodated in various ways known in art, including measures customarily used to condition different rows of 1.5D arrays or in attenuating at VCA stage, adjusting it with apodisation function or simply leaving it as is as a form of apodisation.

The proposed beamformer can be configured to operate in RF-sampling mode or in quadrature (I-Q) sampling mode or in both modes simultaneously.

This beamformer can be used as a stand-alone beamformer of the whole array or be implemented as a sub-aperture beamformer or micro-beamformer with each sub-beamformer working on a separate ADC or be a part or a stage of a larger multilevel beamformer, working as a first stage sub-aperture beamformer or as an intermediate stage beamformer summing the contributions of previous stages and passing the results to the upper stages or as a last stage beamformer outputting the final beamformed RF or I-Q signal to the analog-digital converters. This beamformer also can work as a beamforming stage in combination with any other existing and future beamformer architectures. The beamformer can be connected to transducer elements directly, or via some sub-aperture circuits that combine several neighboring array elements into sub-aperture channels or a "composite element" according to known methods.

The proposed beamformer, fully or in part, can be realized in ASIC or FPGA integrated circuits.

In another embodiment of the proposed beamformer, data acquisition can have two separate modes of operation, namely an economy mode with low power and lower resolution to preserve the battery and a high quality mode with high power and higher spectral and spatial resolutions described above. There in the low power mode, the beamformer would turn off half of its ADCs and elements of the array would be paired such that the aperture would consist of elements connected in twos (refer to FIG. 7) and only half of ADCs will be needed to acquire data.

In another embodiment of the proposed beamformer, while in the low power mode, the beamformer will drop the ADCs clock speed with corresponding drop in channel sampling rates. Dropping ADC clock speed results in lower ADC power consumption, thus in saving the battery while operator is performing initial examination of the area. As soon as diagnostic quality images are needed, the high quality mode can be turned on.

The compact ultrasound imaging system formed according to the present invention may send the beamformed signal to an outside display device wirelessly or wired in a display neutral system or manner.

One advantage of the invention is that it provides significant reduction in the size of the diagnostic ultrasound imaging system such that the hardware build upon reconfigurable ultrasound beamformer architecture can be placed in one or few application specific integrated chips (ASIC) positioned next to the ultrasound array and the whole diagnostic ultrasound imaging system could fit in the handle of the ultrasonic probe while preserving most of the functionality of a cart-based system.

Another advantage of the invention is that such compact system allows sending data and diagnostic images wirelessly to any image display equipped to receive such transmissions or having such a receiver attached to ubiquitous digital data ports such as USB of the display unit.

Another advantage of the invention is that it provides an improved signal-to-noise ratio by drastic reduction in hardware complexity of the signal path from the transducer elements to the digitizer. Such a shortening of the signal path is achieved by making redundant a number of components of the signal path such as analog high voltage and channel multiplexors, signal cable, and connectors used in prior art to connect ultrasound array with signal processing hardware or reducing the number of such components required.

Another advantage of the invention is that it uses lower power per channel, thus, allowing for extended time operation on battery power.

Minimum Phase Error Beamforming Method With Sparse Array

In another embodiment of the proposed beamformer, the knowledge of precise time of channel voltage samples can be used to minimize the focusing delay error (delay quantization error) of the beamformer through judicial selection of elements that would participate in the current beamforming instance (defined as a recurring step in the beamforming algorithm when the system calculates and compensates current propagation delay from the depth specified by the algorithm). Sampling frequency or time between consecutive samples is the most important parameter to determine the focusing delay error (delay quantization error). In "Design of a simplified delay system for ultrasound phased array imaging", IEEE Trans. Son. Ultrason., vol. 41(3), 1984, G. Manes, et al., it is argued that ultrasound system sampling rate should be at least eight times higher than the central frequency of the transducer. Modern systems aim for much higher sampling clock ratio that together with a request for high dynamic range may put unrealistically high demand for the beamforming hardware performance.

The focusing delay errors can be minimized in systems with sampling rates lower even than the criterion stated above. If the time between consecutive samples is large, but the actual sampling period is small and the system knows its precise location in time, as in beamformer examples described elsewhere in this patent, when, for instance, the system could sample a channel at 30 MS/s with 33 ns time between two consecutive samples, but the actual sampling time is 1/240 MHz or 4.2 ns and therefore, the sample position is known with ±2.1 ns precision.

Then, in one embodiment of the proposed beamformer, knowing the precise time of every sample in the channel, the system can reconstruct sample magnitude at the time position specified by the beamforming algorithm by interpolating the consecutive samples.

Figure 16:
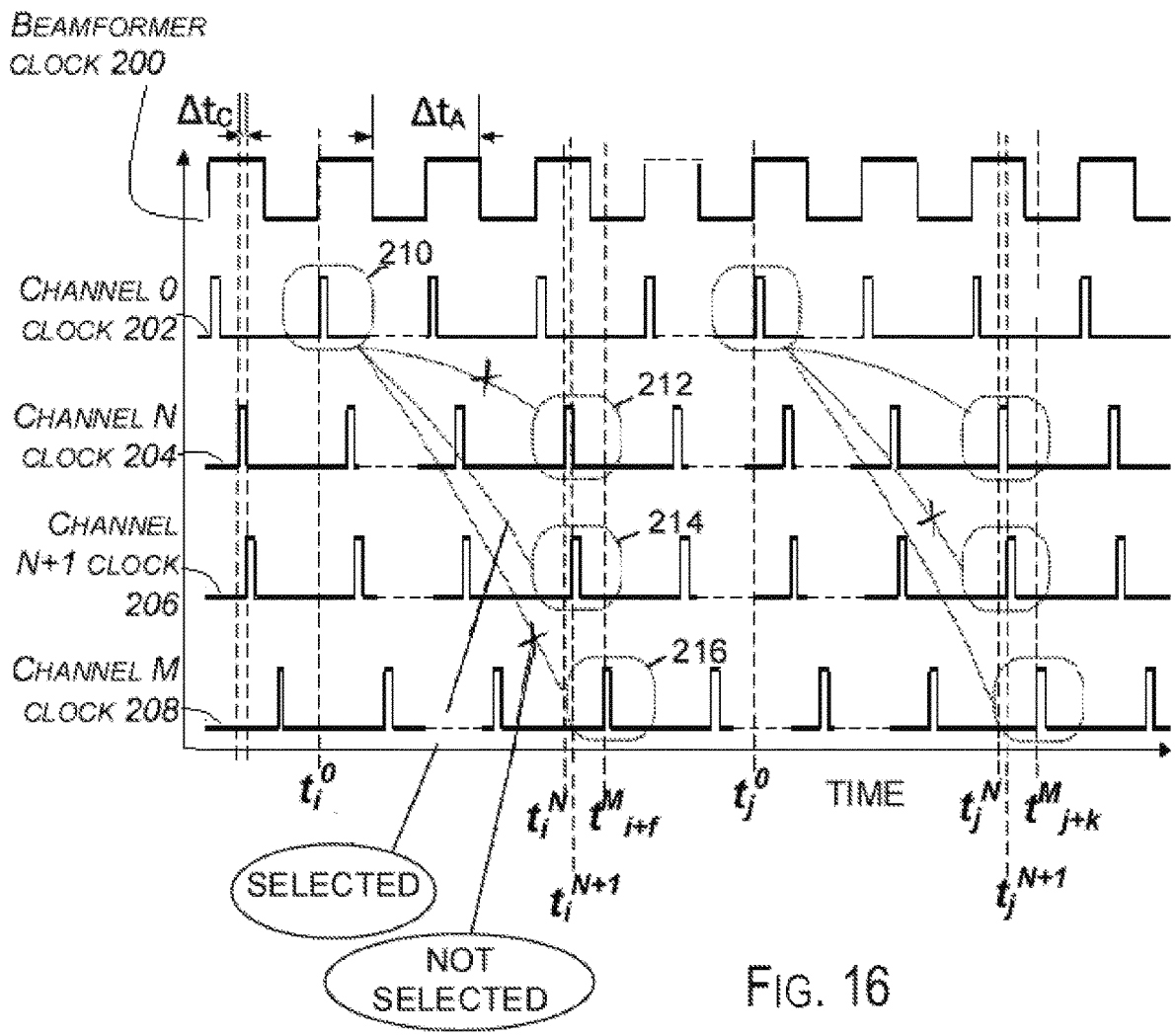
FIG. 16 is an example of time chart illustrating the sparse array beamforming principle to minimize focusing delay errors in accordance with one aspect of the present invention.

In another embodiment of the proposed beamformer, for every beamforming instance, the system can pick only those elements of the array that would have suitable sample with the time difference between the sample time $t_j^N = d_i/c$ where $d_i$ 104 is the distance between the point P 100 and the array's element N 107 and c is the speed of sound and the proper focusing delay $D^N \times \Delta t_C$ less than the allowable delay error $\delta t_E$ (which may be equal to MAPE, for instance): $|t_j^N - D^N \times \Delta t_C| < \delta t_E$, where $D^N$ is the integer delay error increment in the beamforming algorithm for the channel N required to compensate the propagation delay from the current depth. Referring to the timing chart example on FIG. 16, a beamforming clock 200 with period $\Delta t_A = 1/f_S$ when all channels in the active aperture are sampled and channel clocks 202, 204, 206, 208 show each channel sampling time $\Delta t_C = 1/f_{ADC}$. This diagram serves to illustrate the basic working of the sparse array beamforming principle, thus is only intended to schematically reflect the actual timing relationships. To demonstrate this, shown is a time diagram for the element chosen to be the center of the current aperture (element 0) 202, two neighboring elements N 204 and N+1 206 in the aperture at some distance away from the zero element 202 and another more distant element M 208 in the current aperture. At time $t_i$ the beamforming algorithm picks the zero element sample 210 as a base of for the beamforming instance calculation. Next, the samples 212, 214 and 216 are tested for the allowable delay error. In the example in FIG. 16, the $(t_j^N - D^N \times \Delta t_C)$ difference for the samples 212 in channel N and 216 in channel M is bigger than the allowable delay error $\delta t_E$, thus, the system does not use samples of these channels in calculating the current beamforming instance. In another beamforming instance j, the sample from channel N+1 has delay error larger than the system allows, thus, the beamforming sum at that point will not use that sample.

In general this principle may be formulated as follows: in every beamforming instance $t_i$, the system selects for beamforming only elements of array that have delay error $(t_j^N - D^N \times \Delta t_C)$ less that allowable delay error $\delta t_E$ for that particular interrogation point P. Therefore, at every beamforming step the system forms a unique configuration of "active" elements in the current aperture that constitute a sparse array. Even though this method can be applied for 1D or 1.5D arrays, its full benefits can be seen in arrays with large number of elements available for beamforming selection such as in 2D arrays.

This method can be used in any beamformer where actual channel sampling time $\Delta t_C$ is much smaller then aperture sampling time $\Delta t_A$. For instance, if sampling time and sampling period of Sample-and-Hold Circuit (SHC) in front of channel's ADC can be controlled or recorded. Then, the focusing delay error (delay quantization error) of the beamformer is defined not by $\Delta t_A$ but by the smaller sampling time $\Delta t_C$ while the output beamformed data are generated and transferred at lower rate $f_S$ that decrease the performance requirements for the processing hardware. For example, if in a digital beamformer architecture in front of channel's ADC running at 40 MS/s the system may place SHC that samples array element's input at 240 MS/s or if tuning the ADC's internal SHC to that timing, the system delay quantization error will be reduced six times.

The above described invention provides an ultrasound beamforming system and associated method with reconfigurable aperture for an ultrasound imaging system. The method comprising the steps of: A) Providing an ultrasonic array formed of individual ultrasonic array elements configured for transmission and receiving; B) Dividing a subset of the individual array elements into a plurality of individual channels forming an aperture associated with a focal point of a specific depth for a beamforming instance, wherein each channel comprises at least one array element; C) Creating a signal for each channel forming an aperture associated with a focal point of a specific depth for a beamforming instance; D) Sampling, at a sampling rate, the signals of the channels forming an aperture associated with a focal point of a specific depth for a beamforming instance; and E) Reconfiguring the aperture at distinct beamforming instances by at least one of i) Increasing the number of channels forming the aperture at a beam forming instance with an increasing depth of focal point while simultaneously decreasing the sampling rate with an increasing depth of focal point; ii) Increasing the number of array elements that are part of a composite element of a channel forming the aperture at a beam forming instance with an increasing depth of focal point, wherein a composite element is a plurality of individual array elements forming a single channel at a beam forming instance; and iii) Defining allowable delay error for each depth of focal point and selecting a base channel for each beamforming instance to form the aperture and selecting additional channels to form the aperture at the beam forming instance which have a delay error relative to the base channel less than the allowable delay error.

Even though the main area of application of this invention is in medical ultrasound, this beamforming architecture and the hardware and software built upon its principles can be used in other areas such as sonar, radar, robotic vision, terahertz, infrared, optical imaging systems or for seismic geophysical exploration.

It is noteworthy that throughout his document simplified diagrams are shown where many significant actual design blocks and components are omitted for the sake of clarity of the representation, however these omissions are apparent to anyone skilled in art and cannot be considered as flaws of the design. While the application of this method was explained via the standard delay-sum beamforming, it is understood by anyone skilled in art that the same benefits may come by applying this invention for other existing and future beamforming methods including but not limited by the synthetic aperture beamforming and plane wave beamforming.

Although the present invention has been described with particularity herein, the scope of the present invention is not limited to the specific embodiments disclosed. It will be apparent to those of ordinary skill in the art that various modifications in form and details may be made to the present invention without departing from the spirit and scope thereof. It is also expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. An ultrasound beamforming method with reconfigurable aperture for an ultrasound imaging system comprising the steps of:

A) Providing an ultrasonic array formed of individual ultrasonic array elements configured for transmission and receiving;

B) Dividing a subset of the individual array elements into a plurality of individual channels forming an aperture associated with a focal point of a specific depth for a beamforming instance, wherein each channel comprises at least one array element;

C) Creating a signal for each channel forming the aperture associated with the focal point of the specific depth for the beamforming instance;

D) Sampling, at a sampling rate, the signals of the channels forming the aperture associated with the focal point of the specific depth for the beamforming instance;

E) Reconfiguring the aperture at distinct beamforming instances by Increasing the number of channels forming a reconfigured aperture at a separate one of the distinct beam forming instances with an increasing depth of focal point while simultaneously decreasing the sampling rate with an increasing depth of focal point; and F) providing a multiplexor address controller configured to form the reconfigured aperture at the separate one of the distinct beamforming instances from all the individual elements of array and dynamically update the address of the channels forming the reconfigured aperture at the separate one of the distinct beamforming instances that are connected to an analog to digital converter.

2. The ultrasound beamforming method according to claim 1 wherein at a maximum depth of the focal point the beamforming method has maximum number of channels forming the aperture and has a smallest channel sampling rate that is defined by a sampling rate of an analog to digital converter which sampling rate is divided by the number of channels forming the aperture that are connected to analog to digital converter.

3. The ultrasound beamforming method according to claim 1 wherein the multiplexor address controller includes three registers, including a Base Address Register that stores the address of the element at the beginning of the aperture associated with the focal point of the specific depth for the beamforming instance, an Aperture Length Register that holds the number of elements in the aperture associated with the focal point of the specific depth for the beamforming instance and an Address in Aperture Register that holds the element's number that is connected to the analog to digital converter during a current clock cycle.

4. The ultrasound beamforming method according to claim 1 wherein a beam formed by the beamforming method is symmetrical about at least one central array element and wherein the channels forming the aperture associated with the focal point of the specific depth for the beamforming instance other than the channel including the at least one central array elements are each formed of a plurality of elements symmetrically spaced about the at least one central array element.

5. The ultrasound beamforming method according to claim 1 including the step of increasing the number of array elements that are part of a composite element of a channel forming the reconfigured aperture at the separate one of the distinct beam forming instances with an increasing depth of focal point, wherein a composite element is a plurality of individual array elements forming a single channel at the separate one of the distinct beam forming instances.

6. The ultrasound beamforming method according to claim 1 including the step of increasing the number of array elements that are part of a composite element of a channel forming the reconfigured aperture at the separate one of the distinct beam forming instances with an increasing depth of focal point, wherein a composite element is a plurality of individual array elements forming a single channel at the separate one of the distinct beam forming instances.

7. The ultrasound beamforming method according to claim 6 including the step of dynamically controlling aperture position, size and the size of composite elements in the reconfigured aperture to optimize both beamforming channels sampling time with depth of focus.

8. The ultrasound beamforming method according to claim 1 including the step of defining allowable delay error for each depth of focal point and selecting a base channel for each beamforming instance to form the reconfigured aperture and selecting additional channels to form the reconfigured aperture at the separate one of the distinct beam forming instances which have a delay error relative to the base channel less than the allowable delay error.

9. An ultrasound beamforming system with a reconfigurable aperture for an ultrasound imaging comprising:
 an ultrasonic array formed of individual ultrasonic array elements configured for transmission and receiving and
 a control configured for
  A) dividing a subset of the individual array elements into a plurality of individual channels forming an aperture associated with a focal point of a specific depth for a beamforming instance, wherein each channel comprises at least one array element,
  B) Creating a signal for each channel forming the aperture associated with the focal point of the specific depth for the beamforming instance,
  C) Sampling, at a sampling rate, the signals of the channels forming the aperture associated with the focal point of the specific depth for the beamforming instance, and
  E) Reconfiguring the aperture at distinct beamforming instances by Increasing the number of channels forming a reconfigured aperture at a separate one of the beam forming instances with an increasing depth of focal point while simultaneously decreasing the sampling rate with an increasing depth of focal point;
 further including a multiplexor address controller configured to form the reconfigured aperture at the separate one of the beam forming instances from all the individual elements of array and dynamically update the address of the channels forming the reconfigured aperture at the separate one of the beam forming instances that are connected to an analog to digital converter, wherein the multiplexor address controller includes three registers, including a Base Address Register that stores the address of the element at the beginning of the reconfigured aperture, an Aperture Length Register that holds the number of elements in the reconfigured aperture and an Address in Aperture Register that holds the element's number that is connected to the analog to digital converter during a current clock cycle.

10. The ultrasound beamforming system according to claim 9 wherein a beam formed by the beamforming method is symmetrical about at least one central array element and wherein the channels forming the aperture associated with the focal point of the specific depth for the beamforming instance other than the channel including the at least one central array elements are each formed of a plurality of elements symmetrically spaced about the at least one central array element.

11. The ultrasound beamforming system according to claim 9 wherein the size of array's elements varies with the elements position within the array.

12. The ultrasound beamforming system according to claim 9 wherein the controller increases the number of array elements that are part of a composite element of a channel forming the reconfigured aperture at the separate one of the beam forming instances with an increasing depth of focal point, wherein a composite element is a plurality of individual array elements forming a single channel at the separate one of the beam forming instances.

13. The ultrasound beamforming method according to claim 12 wherein the controller dynamically controls aperture position, size and the size of composite elements in the reconfigured aperture to optimize both beamforming channels sampling time with depth of focus.

14. The ultrasound beamforming method according to claim 9 wherein the controller defines an allowable delay error for each depth of focal point and selecting a base channel for each beamforming instance to form the reconfigured aperture and selecting additional channels to form the reconfigured aperture at the separate one of the distinct beam forming instances which have a delay error relative to the base channel less than the allowable delay error.

15. An ultrasound beamforming method with reconfigurable aperture for an ultrasound imaging system comprising the steps of:
 A) Providing an ultrasonic array formed of individual ultrasonic array elements configured for transmission and receiving;
 B) Dividing a subset of the individual array elements into a plurality of individual channels forming an aperture associated with a focal point of a specific depth for a beamforming instance, wherein each channel comprises at least one array element;
 C) Creating a signal for each channel forming the aperture associated with the focal point of the specific depth for the beamforming instance;
 D) Sampling, at a sampling rate, the signals of the channels forming the aperture associated with the focal point of the specific depth for the beamforming instance; and
 E) Dynamically Reconfiguring the aperture at distinct beamforming instances including dynamically controlling aperture position, size and the size of composite elements in the reconfigured aperture to optimize both beamforming channels sampling time with depth of focus including providing a multiplexor address controller configured to form the reconfigured aperture at a separate one of the distinct beamforming instances from all the individual elements of array and dynamically update the address of the channels forming the reconfigured aperture at the separate one of the distinct beamforming instances that are connected to an analog to digital converter.

* * * * *